(12) United States Patent
Greenstein et al.

(10) Patent No.: US 6,863,881 B2
(45) Date of Patent: Mar. 8, 2005

(54) COMPOSITIONS AND METHODS OF NEMATODE CONTROL

(75) Inventors: David Greenstein, Nashville, TN (US); Michael A. Miller, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 10/629,201

(22) Filed: Jul. 29, 2003

(65) Prior Publication Data

US 2004/0045042 A1 Mar. 4, 2004

Related U.S. Application Data

(62) Division of application No. 09/863,063, filed on May 21, 2001, now abandoned.
(60) Provisional application No. 60/274,358, filed on Mar. 8, 2001, and provisional application No. 60/205,829, filed on May 19, 2000.

(51) Int. Cl.$^7$ ................................................ A61K 49/00
(52) U.S. Cl. ..................... 424/9.2; 424/1.11; 424/1.65; 424/9.1
(58) Field of Search ............................... 424/1.11, 1.65, 424/9.2, 9.3, 9.4, 9.6, 9.1; 530/300

(56) References Cited

U.S. PATENT DOCUMENTS

| | | |
|---|---|---|
| 5,023,173 A | 6/1991 | Horwitz et al. |
| 5,432,081 A | 7/1995 | Jefferson |
| 5,599,670 A | 2/1997 | Jefferson |
| 6,057,354 A | 5/2000 | Wu et al. |

OTHER PUBLICATIONS

Klass, et al., *Sperm Isolation and Biochemical Analysis of the Major Sperm Protein from Caenorhabditis Elegans*, Developmental Biology, (1981) 84:299–312.

Ward, S., et al., *The Location of the Major Protein in Caenorhabditis Elegans Sperm and Spermatocytes*, Developmental Biology (1982) 92:203–208.

Mansir, A., et al., *Actin and Major Sperm Protein in Spermatids and Spermatozoa of the Parasitic Nematode Heligmosomoides Polygyrus*, Molecular Reproduction and Development, (1996) 45:332–341.

McCarter, et al., *On the Control Meiotic Maturation and Ovulation in Caenorhabditis Elegans*, Developmental Biology, (1999) 205:111–128.

Database GeneBank, Accession No. CAB54441, Wall, M., Untitled. Y48B6A,5, Direct Submission, Submitted/ Apr. 1, 1999.

Miller, et al., *A Sperm Cytoskeletal Protein That Signals Oocyte Meiotic Maturation and Ovulation*, Science, (Mar. 16, 2001), 291:2144–2147.

C. elegans Sequencing Consortium, *Genome Sequence of the Nematode C. elegans: A Platform for Investigating Biology*, Science, (Dec. 1998) vol. 282, pp. 2012–2018.

*Primary Examiner*—Cameron L. Jones
(74) *Attorney, Agent, or Firm*—Waddey & Patterson, P.C.; I. C. Waddey, Jr.

(57) ABSTRACT

The present invention provides compositions and methods for identifying agents that stimulate or inhibit nematode reproduction, especially related to oocyte maturation, sheath cell contraction, and ovulation. It is disclosed that the major sperm protein (MSP) is acts in signal transduction of female sexual maturation in nematodes. Provided are compositions and methods for identifying anti-nematode agents with MSP as a target and for controlling nematode populations. MSP is an excellent target for identification of anti-nematode factors because it is highly conserved among members of the phylum Nematoda and is not known to exist in other organisms, especially crops, livestock, pets, and humans. Thus, anti-nematode agents that target MSP are less likely to induce severe side effects when administered to a host and the nematode is unlikely to develop resistance to a highly conserved molecule involved in sexual reproduction.

19 Claims, 9 Drawing Sheets

|         |   | 1          10         20         30         40         50         60 |
|---------|---|---|
| MSP-3   | M | AQSVPPGDIQTQPGTKIVFNAPYDDKHTYHIKVINSSARRIGYGIKTTNMKRLGVDPPCGVLDPKEAVL |
| MSP-10  | M | AQSVPPGDIQTQPNAKIVFNAPYDDKHTYHIKVINSSARRIGYGIKTTNMKRLGVDPPCGVLDPKEAVL |
| MSP-19  | M | AQSVPPGDIQTQPGTKIVFNAPYDDKHTYHIKVINSSARRIGYGIKTTNMKRLGVDPPCGVLDPKEAVL |
| MSP-31  | M | AQSVPPGDIQTQPGTKIVFNAPYDDKHTYHIKVINSSARRIGYGIKTTNMKRLGVDPPCGVLDPKEAVL |
| MSP-33  | M | AQSVPPGDIQTQPGTKIVFNAPYDDKHTDHIKVINSSARRIGYGIKTTNMKRLGVDPPCGVLDPKEAVL |
| MSP-38  | M | AQSVPPGDIQTQPGTKIVFNAPYDDKHTYHIKVINSSARRIGYGIKTTNMKRLGVDPPCGVLDPKEAVF |
| MSP-40  | M | AQSVPPGDIQTQPGTKIVFNAPYDDKHTYHIKVINSSARRIGYGIKTTNMKRLGVDPPCGVLDPKEAVL |
| MSP-45  | M | AQSVPPGDIQTQPGTKIVFNAPYDDKHTYHIKVINSSARRIGYGIKTTNMKRLGVDPPCGVLDPKEAVL |
| MSP-49  | M | AQSVPPGDIQTQPGTKIVFNAPYDDKHTYHIKVINSSARRIGYGIKTINMKRLGVDPPCGVLDPKEAVL |
| MSP-50  | M | AQSVPPGDIQTQPGTKIVFNAPYDDKHTYHIKVINSSARRIGYGIKTTNMKRLGVDPPCGVLDPKEAVL |
| MSP-51  | M | AQSVPPGDIQTQPGTKIVFNAPYDDKHTYHIKVINSSARRIGYGLKTTNMKRLGVDPPCGVLDPKEAVL |
| MSP-53  | M | AQSVPPGDIQTQPGTKIVFNAPYDDKHTYHIKVINSSARRIVYGIKTTNMKRLGVDPPCGVLDPKEAVL |
| MSP-55  | M | AQSVPPGDIQTQPGTKIVFNAPYDDKHTYHIKVINSSARRIGYGIKTTNMKRLGVDPPCGVLDPKEAVL |
| MSP-56  | M | AQSVPPGDIQTQPNAKIVFNAPYDDKHTYHIKVINSSARRIVYGIKTTNMKRLGVDPPCGVLDPKEAVL |
| MSP-57  | M | AQSVPPGDIQTQPGTKIVFNAPYDDKHTYHIKVINSSARRIGYGIKTTNMKRLGVDPPCGVLDPKEAVL |
| MSP-59  | M | AQSVPPGDIQTQPGTKIVFNAPYDDKHTYRIKVINSSARRIGYGIKTTNMKRLGVDPPCGVLDPKEAVL |
| MSP-63  | M | AQSVPPGDIQTQPGTKIVFNAPYDDKHTYHIKVINSSARRIGYGIKTTNMKRLGVDPPCGVLDPKEAVL |
| MSP-64  | M | AQSVPPGDIQTQPGTKIVFNAPYDDKHTYHIKVINSSARRIGYGIKTTNMKRLGVDPPCGVLDPKEAVL |
| MSP-65  | M | AQSVPPGDIQTQPGTKIVFNAPYDDKHTYHIKVINSSARRIGYGIKTTNMKRLGVDPPCGVLDPKEAVL |
| MSP-76  | M | AQSVPPGDIQTQPGTKIVFNAPYDDKHTYHIKVINSSARRIGYGIKTTNMKRLGVDPPCGVLDPKEAVL |
| MSP-77  | M | AQSVPPGDIQTQPGTKIVFNAPYDDKHTYHIKVINSSARRIGYGIKTTNMKRLGVDPPCGVLDPKEAVL |
| MSP-78  | M | AQSVPPGDIQTQPGTKIVFNAPYDDKHTYHIKVINSSARRIGYGIKTTNMKRLGVDPPCGVLDPKEAVL |
| MSP-79  | M | AQSVPPGDIQTQPGTKIVFNAPYDDKHTYHIKVINSSARRIGYGIKTTNMKRLGVDPPCGVLDPKEAVL |
| MSP-81  | M | AQSVPPGDIQTQPGTKIVFNAPYDDKHTYHIKVINSSARRIGYGIKTTNMKRLGVDPPCGVLDPKEAVL |
| MSP-113 | M | AQSVPPGDIQTQPGTKIVFNAPYDDKHTYHIKVINSSARRIGYGIKTTNMKRLGVDPPCGVLDPKEAVL |
| MSP-142 | M | AQSVPPGDIQTQPGTKIVFNAPYDDKHTYHIKVINSSARRIGYGIKTTNMKRLGVDPPCGVLDPKEAVL |
| MSP-152 | M | TQSVPPGDIQTQPGTKIVFNAPYDDKHTYHIKVINSSARRIGYGIKTTNMKRLGVDPPCGVLDPKEAVL |

FIG. 6A

|       | 70                                                                                     |   |
|-------|----------------------------------------------------------------------------------------|---|
| MSP-3   | LAVSCDAFAFGQEDTNNDRITVEWTNTPDGAAAKQFRREWFQGDGMVRRKNLPIEYNP | SEQ ID NO:2 |
| MSP-10  | LAVSCDAFAFGQEDTNNDRITVEWTNTPDGAAAKQFRREWFQGDGMVRRKNLPIEYNP | SEQ ID NO:3 |
| MSP-19  | LAVSCDAFAFGQEDTNNDRITVEWTNTPDGAAKQFRREWFQGDGMVRRKNLPIEYNP | SEQ ID NO:1 |
| MSP-31  | LAVSCDAFAFGQEDTNNDRITVEWTNTPDGAAKQFRREWFQGDGMVRRKNLPIEYNP | SEQ ID NO:1 |
| MSP-33  | LAVSCDAFAFGQEDTNNDRITVEWTNTPDGAAKQFRREWFQGDGMVRRKNLPIEYNP | SEQ ID NO:4 |
| MSP-38  | LAVSCDAFAFGQEDTNNDRITVEWTNTPDGAAKQFRREWFQGDGMVRRKNLPIEYNP | SEQ ID NO:5 |
| MSP-40  | LAVSCDAFAFGQEDTNNDRITVEWTNTPDGAAKQFRREWFQGDGMVRRKNLPIEYNP | SEQ ID NO:1 |
| MSP-45  | LAVSCDAFAFGQEDTNNDRITVEWTNTPDGAAKQFRREWFQGDGMVRRKNLPIEYNP | SEQ ID NO:1 |
| MSP-49  | LAVSCDAFAFGQEDTNNDRITVEWTNTPDGAAKQFRREWFQGDGMVRRKNLPIEYNP | SEQ ID NO:6 |
| MSP-50  | LAVSCDAFAFGQEDTNNDRITVEWTNTPDGAAKQFRREWFQGDGMVRRKNLPIEYNP | SEQ ID NO:1 |
| MSP-51  | LAVSCDAFAFGQEDTNNDRITVEWTNTPDGAAKQFRREWFQGDGMVRRKNLPIEYNP | SEQ ID NO:1 |
| MSP-53  | LAVSCDAFAFGQEDTNNDRITVEWTNTPDGAAKQFRREWFQGDGMVRRKNLPIEYNP | SEQ ID NO:1 |
| MSP-55  | LAVSCDAFAFGQEDTNNDRITVEWTNTPDGAAKQFRREWFQGDGMVRRKNLPIEYNP | SEQ ID NO:7 |
| MSP-56  | LAVSCDAFAFGQEDTNNDRITVEWTNTPDGAAKQFRREWFQGDGMVRRKNLPIEYNP | SEQ ID NO:3 |
| MSP-57  | LAVSCDAFAFGQEDTNNDRITVEWTNTPDGAAKQFRREWFQGDGMVRRKNLPIEYNP | SEQ ID NO:7 |
| MSP-59  | LAVSCDAFAFGQEDTNNDRITVEWTNTPDGAAKQFRREWFQGDGMVRRKNLPIEYNP | SEQ ID NO:1 |
| MSP-63  | LAVSCDAFAFGQEDTNNDRITVEWTNTPDGAAKQFRREWFQGDGMVRRKNLPIEYNP | SEQ ID NO:8 |
| MSP-64  | LAVSCDAFAFGQEDTNNDRITVEWTNTPDGAAKQFRREWFQGDGMVRRKNLPIEYNP | SEQ ID NO:1 |
| MSP-65  | LAVSCDAFAFGQEDTNNDRITVEWTNTPDGAAKQFRREWFQGDGMVRRKNLPIEYNP | SEQ ID NO:1 |
| MSP-76  | LAVSCDAFAFGQEDTNNDRITVEWTNTPDGAAKQFRREWFQGDGMVRRKNLPIEYNP | SEQ ID NO:3 |
| MSP-77  | LAVSCDAFAFGQEDTNNDRITVEWTNTPDGAAKQFRREWFQGDGMARRKNLPIEYNP | SEQ ID NO:9 |
| MSP-78  | LAVSCDAFAFGQEDTNNDRITVEWTNTPDGAAKQFRREWFQGDGMVRRKNLPIEYNP | SEQ ID NO:10 |
| MSP-79  | LAVSCDAFAFGQEDTNNDRITVEWTNTPDGAAKQFRREWFQGDGMARRKNLPIEYNP | SEQ ID NO:9 |
| MSP-81  | LAVSCDAFAFGQEDTNNDRITVEWTNTPDGAAKQFRREWFQGDGMVRRKNLPIEYNP | SEQ ID NO:1 |
| MSP-113 | LAVSCDAFAFGQEDTNNDRITVEWTNTPDGAAKQFRREWFQGDGMVRRKNLPIEYNP | SEQ ID NO:1 |
| MSP-142 | LAVSCDAFAFGQEDTNNDRITVEWTNTPDGAAKQFRREWFQGDGMVRRKNLPIEYNP | SEQ ID NO:1 |
| MSP-152 | LAVSCDAFAFGQEDTNNDRITVEWTNTPDGAAKQFRREWFQGDGMVRRKNLPIEYNP | SEQ ID NO:3 |

*FIG. 6B*

```
                1          10         20         30         40         50         60
MSP-142  M      AQSVPPGDIQTQPGTKIVFNAPYDDKHTYHIKVINSSARRIGYYGIKTTNMKRLGVDPPCGVLDPKEAVL
P27439   M      AQSVPPGDINTQPSQKIVFNAPYDDKHTYHIKITNAGGRRIGWAIKTTNMRRLSVDPPCGVLDPKEKVL
P27440   M      AQSVPPGDINTQPGSKIVFNAPYDDKHTYHIKITNAGGRRIGWAIKTTNMRRLGVDPPCGVLDPKESVL 70         80         90        100        110        120    126
MSP-142  LAVSCDAFAFQEDTNNDRITVEWTNTPDGAAKQFRREWFQGDGMVRRKNLPIEYNP  SEQ ID NO:1
P27439   MAVSCDTFNAATEDLNNDRITIEWTNTPDGAAKQFRREWFQGDGMVRRKNLPIEYNL  SEQ ID NO:11
P27440   MAVSCDTFNAATEDLNNDRITIEWTNTPDGAAKQFRREWFQGDGMVRRKNLPIEYNL  SEQ ID NO:12
```

FIG. 7

```
              106     110            120    126
               ↓      ↓              ↓      ↓
    AsMSPα    R EWFQGDGMVRRKNLPIEYN L
    AsMSPβ    R EWFQGDGMVRRKNLPIEYN L
    GrMSP1    L EWFQGDGMVRRKNLPIEYN V
    GrMSP2    L EWFQGDGMVRRKNLPIEYN V
    GrMSP3    L EWFQGDGMVRRKNLPIEYN V
    CeMSP142  R EWFQGDGMVRRKNLPIEYN P
    CeMSP33   R EWFQGDGMVRRKNLPIEYN P
    OvMSP1    R EWFQGDGMVRRKNLPIEYN L
    OvMSP2    R EWFQGDGMVRRKNLPIEYN L
```

FIG. 9

SEQUENCE LISTING

<160> NUMBER OF SEQ ID NOS: 33

<210> SEQ ID NO 1
<211> LENGTH: 126
<212> TYPE: PRT
<213> ORGANISM: Caenorhabditis elegans

<400> SEQUENCE: 1

```
Ala Gln Ser Val Pro Pro Gly Asp Ile Gln Thr Gln Pro Gly Thr Lys
  1               5                  10                  15

Ile Val Phe Asn Ala Pro Tyr Asp Asp Lys His Thr Tyr His Ile Lys
             20                  25                  30

Val Ile Asn Ser Ser Ala Arg Arg Ile Gly Tyr Gly Ile Lys Thr Thr
         35                  40                  45

Asn Met Lys Arg Leu Gly Val Asp Pro Pro Cys Gly Val Leu Asp Pro
 50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
             85                  90                  95

Pro Asp Gly Ala Ala Lys Gln Phe Arg Arg Glu Trp Phe Gln Gly Asp
            100                 105                 110

Gly Met Val Arg Arg Lys Asn Leu Pro Ile Glu Tyr Asn Pro
        115                 120                 125
```

<210> SEQ ID NO 2
<211> LENGTH: 126
<212> TYPE: PRT
<213> ORGANISM: Caenorhabditis elegans

<400> SEQUENCE: 2

```
Ala Gln Ser Val Pro Pro Gly Asp Ile Gln Thr Gln Pro Gly Thr Lys
  1               5                  10                  15

Ile Val Phe Asn Ala Pro Tyr Asp Asp Lys His Thr Tyr His Ile Lys
             20                  25                  30

Val Ile Asn Ser Ser Ala Arg Arg Ile Gly Tyr Gly Ile Lys Thr Thr
         35                  40                  45
```

```
Asn Met Lys Arg Leu Gly Val Asp Pro Pro Cys Gly Val Leu Asp Pro
        50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Arg Gln Phe Arg Arg Glu Trp Phe Gln Gly Asp
               100                 105                 110

Gly Met Val Arg Arg Lys Asn Leu Pro Ile Glu Tyr Asn Pro
           115                 120                 125

<210> SEQ ID NO 3
<211> LENGTH: 126
<212> TYPE: PRT
<213> ORGANISM: Caenorhabditis elegans

<400> SEQUENCE: 3

Ala Gln Ser Val Pro Pro Gly Asp Ile Gln Thr Gln Pro Asn Ala Lys
 1               5                  10                  15

Ile Val Phe Asn Ala Pro Tyr Asp Asp Lys His Thr Tyr His Ile Lys
                20                  25                  30

Val Ile Asn Ser Ser Ala Arg Arg Ile Gly Tyr Gly Ile Lys Thr Thr
            35                  40                  45

Asn Met Lys Arg Leu Gly Val Asp Pro Pro Cys Gly Val Leu Asp Pro
        50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
               100                 105                 110

Gly Met Val Arg Arg Lys Asn Leu Pro Ile Glu Tyr Asn Pro
           115                 120                 125

<210> SEQ ID NO 4
<211> LENGTH: 126
<212> TYPE: PRT
<213> ORGANISM: Caenorhabditis elegans

<400> SEQUENCE: 4

Ala Gln Ser Val Pro Pro Gly Asp Ile Gln Thr Gln Pro Asn Ala Lys
 1               5                  10                  15

Ile Val Phe Asn Ala Pro Tyr Asp Asp Lys His Thr Tyr His Ile Lys
                20                  25                  30

Val Ile Asn Ser Ser Ala Arg Arg Ile Gly Tyr Gly Ile Lys Thr Thr
            35                  40                  45

Asn Met Lys Arg Leu Gly Val Asp Pro Pro Cys Gly Val Leu Asp Pro
        50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
               100                 105                 110

Gly Met Val Arg Arg Lys Asn Leu Pro Ile Glu Tyr Asn Pro
           115                 120                 125
```

```
<210> SEQ ID NO 5
<211> LENGTH: 126
<212> TYPE: PRT
<213> ORGANISM: Caenorhabditis elegans

<400> SEQUENCE: 5

Ala Gln Ser Val Pro Pro Gly Asp Ile Gln Thr Gln Pro Gly Thr Lys
 1               5                  10                  15

Ile Val Phe Asn Ala Pro Tyr Asp Asp Lys His Thr Asp His Ile Lys
            20                  25                  30

Val Ile Asn Ser Ser Ala Arg Arg Ile Gly Tyr Gly Ile Lys Thr Thr
        35                  40                  45

Asn Met Lys Arg Leu Gly Val Asp Pro Pro Cys Gly Val Phe Asp Pro
 50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
            100                 105                 110

Gly Met Val Arg Arg Lys Asn Leu Pro Ile Glu Tyr Asn Pro
        115                 120                 125

<210> SEQ ID NO 6
<211> LENGTH: 126
<212> TYPE: PRT
<213> ORGANISM: Caenorhabditis elegans

<400> SEQUENCE: 6

Ala Gln Ser Val Pro Pro Gly Asp Ile Gln Thr Gln Pro Gly Thr Lys
 1               5                  10                  15

Ile Val Phe Asn Ala Pro Tyr Asp Asp Lys His Thr Tyr His Ile Lys
            20                  25                  30

Val Ile Asn Ser Ser Ala Arg Arg Ile Gly Tyr Gly Ile Lys Thr Ile
        35                  40                  45

Asn Met Lys Arg Leu Gly Val Asp Pro Pro Cys Gly Val Leu Asp Pro
 50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
            100                 105                 110

Gly Met Val Arg Arg Lys Asn Leu Pro Ile Glu Tyr Asn Pro
        115                 120                 125

<210> SEQ ID NO 7
<211> LENGTH: 126
<212> TYPE: PRT
<213> ORGANISM: Caenorhabditis elegans

<400> SEQUENCE: 7

Ala Gln Ser Val Pro Pro Gly Asp Ile Gln Thr Gln Pro Gly Thr Lys
 1               5                  10                  15

Ile Val Phe Asn Ala Pro Tyr Asp Asp Lys His Thr Tyr His Ile Lys
            20                  25                  30
```

-continued

```
Val Ile Asn Ser Ser Ala Arg Arg Ile Val Tyr Gly Ile Lys Thr Thr
            35                  40                  45

Asn Met Lys Arg Leu Gly Val Asp Pro Pro Cys Gly Val Leu Asp Pro
        50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
            100                 105                 110

Gly Met Val Arg Arg Lys Asn Leu Pro Ile Glu Tyr Asn Pro
        115                 120                 125
```

<210> SEQ ID NO 8
<211> LENGTH: 126
<212> TYPE: PRT
<213> ORGANISM: Caenorhabditis elegans

<400> SEQUENCE: 8

```
Ala Gln Ser Val Pro Pro Gly Asp Ile Gln Thr Gln Pro Gly Thr Lys
 1                   5                  10                  15

Ile Val Phe Asn Ala Pro Tyr Asp Asp Lys His Thr Tyr Arg Ile Lys
                20                  25                  30

Val Ile Asn Ser Ser Ala Arg Arg Ile Gly Tyr Gly Ile Lys Thr Thr
            35                  40                  45

Asn Met Lys Arg Leu Gly Val Asp Pro Pro Cys Gly Val Leu Asp Pro
        50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
            100                 105                 110

Gly Met Val Arg Arg Lys Asn Leu Pro Ile Glu Tyr Asn Pro
        115                 120                 125
```

<210> SEQ ID NO 9
<211> LENGTH: 126
<212> TYPE: PRT
<213> ORGANISM: Caenorhabditis elegans

<400> SEQUENCE: 9

```
Ala Gln Ser Val Pro Pro Gly Asp Ile Gln Thr Gln Pro Gly Thr Lys
 1                   5                  10                  15

Ile Val Phe Asn Ala Pro Tyr Asp Asp Lys His Thr Tyr His Ile Lys
                20                  25                  30

Val Ile Asn Ser Ser Ala Arg Arg Ile Gly Tyr Gly Ile Lys Thr Thr
            35                  40                  45

Asn Met Lys Arg Leu Gly Val Asp Pro Pro Cys Gly Val Leu Asp Pro
        50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Val Glu Trp Thr Asn Thr
                85                  90                  95

Pro Asp Gly Ala Ala Lys Gln Phe Arg Arg Glu Trp Phe Gln Gly Asp
            100                 105                 110
```

```
Gly Met Ala Arg Arg Lys Asn Leu Pro Ile Glu Tyr Asn Pro
        115                 120                 125
```

<210> SEQ ID NO 10
<211> LENGTH: 126
<212> TYPE: PRT
<213> ORGANISM: Caenorhabditis elegans

<400> SEQUENCE: 10

```
Ala Gln Ser Val Pro Pro Gly Asp Ile Gln Thr Gln Pro Gly Thr Lys
  1               5                  10                  15

Ile Val Phe Asn Ala Pro Tyr Asp Asp Lys His Thr Tyr His Ile Lys
                 20                  25                  30

Val Ile Asn Ser Ser Ala Arg Arg Ile Gly Tyr Gly Ile Lys Thr Thr
             35                  40                  45

Asn Met Lys Arg Leu Gly Val Asp Pro Pro Cys Gly Val Leu Asp Pro
         50                  55                  60

Lys Glu Ala Val Leu Leu Ala Val Ser Cys Asp Ala Phe Ala Phe Gly
 65                  70                  75                  80

Gln Glu Asp Thr Asn Asn Asp Arg Ile Thr Ile Glu Trp Thr Asn Thr
                 85                  90                  95

Pro Asp Gly Ala Ala Lys Gln Phe Arg Arg Glu Trp Phe Gln Gly Asp
                100                 105                 110

Gly Met Val Arg Arg Lys Asn Leu Pro Ile Glu Tyr Asn Pro
        115                 120                 125
```

<210> SEQ ID NO 11
<211> LENGTH: 126
<212> TYPE: PRT
<213> ORGANISM: Ascaris suum

<400> SEQUENCE: 11

```
Ala Gln Ser Val Pro Pro Gly Asp Ile Asn Thr Gln Pro Ser Gln Lys
  1               5                  10                  15

Ile Val Phe Asn Ala Pro Tyr Asp Asp Lys His Thr Tyr His Ile Lys
                 20                  25                  30

Ile Thr Asn Ala Gly Gly Arg Arg Ile Gly Trp Ala Ile Lys Thr Thr
             35                  40                  45

Asn Met Arg Arg Leu Ser Val Asp Pro Pro Cys Gly Val Leu Asp Pro
         50                  55                  60

Lys Glu Lys Val Leu Met Ala Val Ser Cys Asp Thr Phe Asn Ala Ala
 65                  70                  75                  80

Thr Glu Asp Leu Asn Asn Asp Arg Ile Thr Ile Glu Trp Thr Asn Thr
                 85                  90                  95

Pro Asp Gly Ala Ala Lys Gln Phe Arg Arg Glu Trp Phe Gln Gly Asp
                100                 105                 110

Gly Met Val Arg Arg Lys Asn Leu Pro Ile Glu Tyr Asn Leu
        115                 120                 125
```

<210> SEQ ID NO 12
<211> LENGTH: 126
<212> TYPE: PRT
<213> ORGANISM: Ascaris suum

<400> SEQUENCE: 12

```
Ala Gln Ser Val Pro Pro Gly Asp Ile Asn Thr Gln Pro Gly Ser Lys
  1               5                  10                  15

Ile Val Phe Asn Ala Pro Tyr Asp Asp Lys His Thr Tyr His Ile Lys
```

-continued

```
                20                  25                  30
Ile Thr Asn Ala Gly Gly Arg Arg Ile Gly Trp Ala Ile Lys Thr Thr
            35                  40                  45
Asn Met Arg Arg Leu Gly Val Asp Pro Pro Cys Gly Val Leu Asp Pro
        50                  55                  60
Lys Glu Ser Val Leu Met Ala Val Ser Cys Asp Thr Phe Asn Ala Ala
65                  70                  75                  80
Thr Glu Asp Leu Asn Asn Asp Arg Ile Thr Ile Glu Trp Thr Asn Thr
                85                  90                  95
Pro Asp Gly Ala Ala Lys Gln Phe Arg Arg Glu Trp Phe Gln Gly Asp
            100                 105                 110
Gly Met Val Arg Arg Lys Asn Leu Pro Ile Glu Tyr Asn Leu
        115                 120                 125

<210> SEQ ID NO 13
<211> LENGTH: 21
<212> TYPE: PRT
<213> ORGANISM: Ascaris suum
<220> FEATURE:
<223> OTHER INFORMATION: MSP-alpha

<400> SEQUENCE: 13

Arg Glu Trp Phe Gln Gly Asp Gly Met Val Arg Arg Lys Asn Leu Pro
1               5                   10                  15
Ile Glu Tyr Asn Leu
            20

<210> SEQ ID NO 14
<211> LENGTH: 21
<212> TYPE: PRT
<213> ORGANISM: Ascaris suum
<220> FEATURE:
<223> OTHER INFORMATION: MSP-beta

<400> SEQUENCE: 14

Arg Glu Trp Phe Gln Gly Asp Gly Met Val Arg Arg Lys Asn Leu Pro
1               5                   10                  15
Ile Glu Tyr Asn Leu
            20

<210> SEQ ID NO 15
<211> LENGTH: 21
<212> TYPE: PRT
<213> ORGANISM: Globodera rostochiensis
<220> FEATURE:
<223> OTHER INFORMATION: MSP1

<400> SEQUENCE: 15

Leu Glu Trp Phe Gln Gly Asp Gly Met Val Arg Arg Lys Asn Leu Pro
1               5                   10                  15
Ile Glu Tyr Asn Val
            20

<210> SEQ ID NO 16
<211> LENGTH: 21
<212> TYPE: PRT
<213> ORGANISM: Globodera rostochiensis
<220> FEATURE:
<223> OTHER INFORMATION: MSP2

<400> SEQUENCE: 16

Leu Glu Trp Phe Gln Gly Asp Gly Met Val Arg Arg Lys Asn Leu Pro
```

```
                1               5              10              15

Ile Glu Tyr Asn Val
            20

<210> SEQ ID NO 17
<211> LENGTH: 21
<212> TYPE: PRT
<213> ORGANISM: Globodera rostochiensis
<220> FEATURE:
<223> OTHER INFORMATION: MSP3

<400> SEQUENCE: 17

Arg Glu Trp Phe Gln Gly Asp Gly Met Ala Arg Arg Lys Asn Leu Pro
  1               5                  10                  15

Ile Glu Tyr Asn Pro
            20

<210> SEQ ID NO 18
<211> LENGTH: 21
<212> TYPE: PRT
<213> ORGANISM: Caenorhabditis elegans
<220> FEATURE:
<223> OTHER INFORMATION: MSP142

<400> SEQUENCE: 18

Arg Glu Trp Phe Gln Gly Asp Gly Met Ala Arg Arg Lys Asn Leu Pro
  1               5                  10                  15

Ile Glu Tyr Asn Pro
            20

<210> SEQ ID NO 19
<211> LENGTH: 21
<212> TYPE: PRT
<213> ORGANISM: Caenorhabditis elegans
<220> FEATURE:
<223> OTHER INFORMATION: MSP33

<400> SEQUENCE: 19

Arg Glu Trp Phe Gln Gly Asp Gly Met Ala Arg Arg Lys Asn Leu Pro
  1               5                  10                  15

Ile Glu Tyr Asn Leu
            20

<210> SEQ ID NO 20
<211> LENGTH: 21
<212> TYPE: PRT
<213> ORGANISM: Onchocerca volvulus
<220> FEATURE:
<223> OTHER INFORMATION: MSP1

<400> SEQUENCE: 20

Arg Glu Trp Phe Gln Gly Asp Gly Met Ala Arg Arg Lys Asn Leu Pro
  1               5                  10                  15

Ile Glu Tyr Asn Leu
            20

<210> SEQ ID NO 21
<211> LENGTH: 127
<212> TYPE: PRT
<213> ORGANISM: Onchocerca volvulus
<220> FEATURE:
<223> OTHER INFORMATION: MSP2

<400> SEQUENCE: 21
```

-continued

```
Met Ala Gln Ser Val Pro Gly Asp Ile Gln Thr Gln Pro Gly Thr
 1               5                  10                  15

Lys Ile Val Phe Asn Ala Pro Tyr Asp Asp Lys His Thr Tyr His Ile
                 20                  25                  30

Lys Val Ile Asn Ser Ser Ala Arg Arg Ile Gly Tyr Gly Ile Lys Thr
             35                  40                  45

Thr Asn Met Lys Arg Leu Gly Val Asp Pro Pro Cys Gly Val Leu Asp
         50                  55                  60

Pro Lys Glu Ala Val Leu Leu Ala Val Ser Cys Asp Ala Phe Ala Phe
 65                  70                  75                  80

Gly Gln Glu Asp Thr Asn Asn Asp Arg Ile Thr Val Glu Trp Thr Asn
                     85                  90                  95

Thr Pro Asp Gly Ala Ala Lys Gln Phe Arg Arg Glu Trp Phe Gln Gly
             100                 105                 110

Asp Gly Met Val Arg Arg Lys Asn Leu Pro Ile Glu Tyr Asn Pro
             115                 120                 125
```

<210> SEQ ID NO 22
<211> LENGTH: 127
<212> TYPE: PRT
<213> ORGANISM: Caenorhabditis elegans

<400> SEQUENCE: 22

```
Met Ala Gln Ser Val Pro Gly Asp Ile Gln Thr Gln Pro Gly Thr
 1               5                  10                  15

Lys Ile Val Phe Asn Ala Pro Tyr Asp Asp Lys His Thr Tyr His Ile
                 20                  25                  30

Lys Val Ile Asn Ser Ser Ala Arg Arg Ile Gly Tyr Gly Ile Lys Thr
             35                  40                  45

Thr Asn Met Lys Arg Leu Gly Val Asp Pro Pro Cys Gly Val Leu Asp
         50                  55                  60

Pro Lys Glu Ala Val Leu Leu Ala Val Ser Cys Asp Ala Phe Ala Phe
 65                  70                  75                  80

Gly Gln Glu Asp Thr Asn Asn Asp Arg Ile Thr Val Glu Trp Thr Asn
                     85                  90                  95

Thr Pro Asp Gly Ala Ala Arg Gln Phe Arg Arg Glu Trp Phe Gln Gly
             100                 105                 110

Asp Gly Met Val Arg Arg Lys Asn Leu Pro Ile Glu Tyr Asn Pro
             115                 120                 125
```

<210> SEQ ID NO 23
<211> LENGTH: 127
<212> TYPE: PRT
<213> ORGANISM: Caenorhabditis elegans

<400> SEQUENCE: 23

```
Met Ala Gln Ser Val Pro Gly Asp Ile Gln Thr Gln Pro Asn Ala
 1               5                  10                  15

Lys Ile Val Phe Asn Ala Pro Tyr Asp Asp Lys His Thr Tyr His Ile
                 20                  25                  30

Lys Val Ile Asn Ser Ser Ala Arg Arg Ile Gly Tyr Gly Ile Lys Thr
             35                  40                  45

Thr Asn Met Lys Arg Leu Gly Val Asp Pro Pro Cys Gly Val Leu Asp
         50                  55                  60

Pro Lys Glu Ala Val Leu Leu Ala Val Ser Cys Asp Ala Phe Ala Phe
 65                  70                  75                  80
```

```
Gly Gln Glu Asp Thr Asn Asn Asp Arg Ile Thr Val Glu Trp Thr Asn
                 85                  90                  95

Thr Pro Asp Gly Ala Ala Lys Gln Phe Arg Arg Glu Trp Phe Gln Gly
            100                 105                 110

Asp Gly Met Val Arg Arg Lys Asn Leu Pro Ile Glu Tyr Asn Pro
        115                 120                 125

<210> SEQ ID NO 24
<211> LENGTH: 127
<212> TYPE: PRT
<213> ORGANISM: Caenorhabditis elegans

<400> SEQUENCE: 24

Met Ala Gln Ser Val Pro Pro Gly Asp Ile Gln Thr Gln Pro Asn Ala
  1               5                  10                  15

Lys Ile Val Phe Asn Ala Pro Tyr Asp Asp Lys His Thr Tyr His Ile
                 20                  25                  30

Lys Val Ile Asn Ser Ser Ala Arg Arg Ile Gly Tyr Gly Ile Lys Thr
             35                  40                  45

Thr Asn Met Lys Arg Leu Gly Val Asp Pro Pro Cys Gly Val Leu Asp
         50                  55                  60

Pro Lys Glu Ala Val Leu Leu Ala Val Ser Cys Asp Ala Phe Ala Phe
 65                  70                  75                  80

Gly Gln Glu Asp Thr Asn Asn Asp Arg Ile Thr Val Glu Trp Thr Asn
                 85                  90                  95

Thr Pro Asp Gly Ala Ala Lys Gln Phe Arg Arg Glu Trp Phe Gln Gly
            100                 105                 110

Asp Gly Met Val Arg Arg Lys Asn Leu Pro Ile Glu Tyr Asn Pro
        115                 120                 125

<210> SEQ ID NO 25
<211> LENGTH: 127
<212> TYPE: PRT
<213> ORGANISM: Caenorhabditis elegans

<400> SEQUENCE: 25

Met Ala Gln Ser Val Pro Pro Gly Asp Ile Gln Thr Gln Pro Gly Thr
  1               5                  10                  15
Lys Ile Val Phe Asn Ala Pro Tyr Asp Asp Lys His Thr Asp His Ile
                 20                  25                  30
Lys Val Ile Asn Ser Ser Ala Arg Arg Ile Gly Tyr Gly Ile Lys Thr
             35                  40                  45
Thr Asn Met Lys Arg Leu Gly Val Asp Pro Pro Cys Gly Val Phe Asp
         50                  55                  60
Pro Lys Glu Ala Val Leu Leu Ala Val Ser Cys Asp Ala Phe Ala Phe
 65                  70                  75                  80
Gly Gln Glu Asp Thr Asn Asn Asp Arg Ile Thr Val Glu Trp Thr Asn
                 85                  90                  95
Thr Pro Asp Gly Ala Ala Lys Gln Phe Arg Arg Glu Trp Phe Gln Gly
            100                 105                 110
Asp Gly Met Val Arg Arg Lys Asn Leu Pro Ile Glu Tyr Asn Pro
        115                 120                 125

<210> SEQ ID NO 26
<211> LENGTH: 127
<212> TYPE: PRT
<213> ORGANISM: Caenorhabditis elegans

<400> SEQUENCE: 26

Met Ala Gln Ser Val Pro Pro Gly Asp Ile Gln Thr Gln Pro Gly Thr
  1               5                  10                  15

Lys Ile Val Phe Asn Ala Pro Tyr Asp Asp Lys His Thr Tyr His Ile
                 20                  25                  30
```

```
Lys Val Ile Asn Ser Ser Ala Arg Arg Ile Gly Tyr Gly Ile Lys Thr
            35                  40                  45
Ile Asn Met Lys Arg Leu Gly Val Asp Pro Pro Cys Gly Val Leu Asp
 50                  55                  60
Pro Lys Glu Ala Val Leu Leu Ala Val Ser Cys Asp Ala Phe Ala Phe
 65                  70                  75                  80
Gly Gln Glu Asp Thr Asn Asn Asp Arg Ile Thr Val Glu Trp Thr Asn
                 85                  90                  95
Thr Pro Asp Gly Ala Ala Lys Gln Phe Arg Arg Glu Trp Phe Gln Gly
                100                 105                 110
Asp Gly Met Val Arg Arg Lys Asn Leu Pro Ile Glu Tyr Asn Pro
            115                 120                 125

<210> SEQ ID NO 27
<211> LENGTH: 127
<212> TYPE: PRT
<213> ORGANISM: Caenorhabditis elegans

<400> SEQUENCE: 27

Met Ala Gln Ser Val Pro Pro Gly Asp Ile Gln Thr Gln Pro Gly Thr
  1               5                  10                  15
Lys Ile Val Phe Asn Ala Pro Tyr Asp Asp Lys His Thr Tyr His Ile
             20                  25                  30
Lys Val Ile Asn Ser Ser Ala Arg Arg Ile Val Tyr Gly Ile Lys Thr
            35                  40                  45
Thr Asn Met Lys Arg Leu Gly Val Asp Pro Pro Cys Gly Val Leu Asp
 50                  55                  60
Pro Lys Glu Ala Val Leu Leu Ala Val Ser Cys Asp Ala Phe Ala Phe
 65                  70                  75                  80
Gly Gln Glu Asp Thr Asn Asn Asp Arg Ile Thr Val Glu Trp Thr Asn
                 85                  90                  95
Thr Pro Asp Gly Ala Ala Lys Gln Phe Arg Arg Glu Trp Phe Gln Gly
                100                 105                 110
Asp Gly Met Val Arg Arg Lys Asn Leu Pro Ile Glu Tyr Asn Pro
            115                 120                 125

<210> SEQ ID NO 28
<211> LENGTH: 127
<212> TYPE: PRT
<213> ORGANISM: Caenorhabditis elegans

<400> SEQUENCE: 28

Met Ala Gln Ser Val Pro Pro Gly Asp Ile Gln Thr Gln Pro Gly Thr
  1               5                  10                  15
Lys Ile Val Phe Asn Ala Pro Tyr Asp Asp Lys His Thr Tyr Arg Ile
             20                  25                  30
Lys Val Ile Asn Ser Ser Ala Arg Arg Ile Gly Tyr Gly Ile Lys Thr
            35                  40                  45
Thr Asn Met Lys Arg Leu Gly Val Asp Pro Pro Cys Gly Val Leu Asp
 50                  55                  60
Pro Lys Glu Ala Val Leu Leu Ala Val Ser Cys Asp Ala Phe Ala Phe
 65                  70                  75                  80
Gly Gln Glu Asp Thr Asn Asn Asp Arg Ile Thr Val Glu Trp Thr Asn
                 85                  90                  95
Thr Pro Asp Gly Ala Ala Lys Gln Phe Arg Arg Glu Trp Phe Gln Gly
                100                 105                 110
```

Asp Gly Met Val Arg Arg Lys Asn Leu Pro Ile Glu Tyr Asn Pro
        115                 120                 125

<210> SEQ ID NO 29
<211> LENGTH: 127
<212> TYPE: PRT
<213> ORGANISM: Caenorhabditis elegans

<400> SEQUENCE: 29

Met Ala Gln Ser Val Pro Pro Gly Asp Ile Gln Thr Gln Pro Gly Thr
  1               5                  10                  15

Lys Ile Val Phe Asn Ala Pro Tyr Asp Asp Lys His Thr Tyr His Ile
             20                  25                  30

Lys Val Ile Asn Ser Ser Ala Arg Arg Ile Gly Tyr Gly Ile Lys Thr
         35                  40                  45

Thr Asn Met Lys Arg Leu Gly Val Asp Pro Pro Cys Gly Val Leu Asp
     50                  55                  60

Pro Lys Glu Ala Val Leu Leu Ala Val Ser Cys Asp Ala Phe Ala Phe
 65                  70                  75                  80

Gly Gln Glu Asp Thr Asn Asn Asp Arg Ile Thr Val Glu Trp Thr Asn
                 85                  90                  95

Thr Pro Asp Gly Ala Ala Lys Gln Phe Arg Arg Glu Trp Phe Gln Gly
            100                 105                 110

Asp Gly Met Ala Arg Arg Lys Asn Leu Pro Ile Glu Tyr Asn Pro
        115                 120                 125

<210> SEQ ID NO 30
<211> LENGTH: 127
<212> TYPE: PRT
<213> ORGANISM: Caenorhabditis elegans

<400> SEQUENCE: 30

Met Ala Gln Ser Val Pro Pro Gly Asp Ile Gln Thr Gln Pro Gly Thr
  1               5                  10                  15

Lys Ile Val Phe Asn Ala Pro Tyr Asp Asp Lys His Thr Tyr His Ile
             20                  25                  30

Lys Val Ile Asn Ser Ser Ala Arg Arg Ile Gly Tyr Gly Ile Lys Thr
         35                  40                  45

Thr Asn Met Lys Arg Leu Gly Val Asp Pro Pro Cys Gly Val Leu Asp
     50                  55                  60

Pro Lys Glu Ala Val Leu Leu Ala Val Ser Cys Asp Ala Phe Ala Phe
 65                  70                  75                  80

Gly Gln Glu Asp Thr Asn Asn Asp Arg Ile Thr Ile Glu Trp Thr Asn
                 85                  90                  95

Thr Pro Asp Gly Ala Ala Lys Gln Phe Arg Arg Glu Trp Phe Gln Gly
            100                 105                 110

Asp Gly Met Val Arg Arg Lys Asn Leu Pro Ile Glu Tyr Asn Pro
        115                 120                 125

<210> SEQ ID NO 31
<211> LENGTH: 127
<212> TYPE: PRT
<213> ORGANISM: Caenorhabditis elegans

<400> SEQUENCE: 31

Met Ala Gln Ser Val Pro Pro Gly Asp Ile Asn Thr Gln Pro Ser Gln
  1               5                  10                  15

-continued

```
Lys Ile Val Phe Asn Ala Pro Tyr Asp Asp Lys His Thr Tyr His Ile
            20                  25                  30
Lys Ile Thr Asn Ala Gly Gly Arg Arg Ile Gly Trp Ala Ile Lys Thr
        35                  40                  45
Thr Asn Met Arg Arg Leu Ser Val Asp Pro Pro Cys Gly Val Leu Asp
    50                  55                  60
Pro Lys Glu Lys Val Leu Met Ala Val Ser Cys Asp Thr Phe Asn Ala
65                  70                  75                  80
Ala Thr Glu Asp Leu Asn Asn Asp Arg Ile Thr Ile Glu Trp Thr Asn
                85                  90                  95
Thr Pro Asp Gly Ala Ala Lys Gln Phe Arg Arg Glu Trp Phe Gln Gly
            100                 105                 110
Asp Gly Met Val Arg Arg Lys Asn Leu Pro Ile Glu Tyr Asn Leu
        115                 120                 125
```

<210> SEQ ID NO 32
<211> LENGTH: 127
<212> TYPE: PRT
<213> ORGANISM: Caenorhabditis elegans

<400> SEQUENCE: 32

```
Met Ala Gln Ser Val Pro Pro Gly Asp Ile Asn Thr Gln Pro Gly Ser
1               5                   10                  15
Lys Ile Val Phe Asn Ala Pro Tyr Asp Asp Lys His Thr Tyr His Ile
            20                  25                  30
Lys Ile Thr Asn Ala Gly Gly Arg Arg Ile Gly Trp Ala Ile Lys Thr
        35                  40                  45
Thr Asn Met Arg Arg Leu Gly Val Asp Pro Pro Cys Gly Val Leu Asp
    50                  55                  60
Pro Lys Glu Ser Val Leu Met Ala Val Ser Cys Asp Thr Phe Asn Ala
65                  70                  75                  80
Ala Thr Glu Asp Leu Asn Asn Asp Arg Ile Thr Ile Glu Trp Thr Asn
                85                  90                  95
Thr Pro Asp Gly Ala Ala Lys Gln Phe Arg Arg Glu Trp Phe Gln Gly
            100                 105                 110
Asp Gly Met Val Arg Arg Lys Asn Leu Pro Ile Glu Tyr Asn Leu
        115                 120                 125
```

<210> SEQ ID NO 33
<211> LENGTH: 127
<212> TYPE: PRT
<213> ORGANISM: Caenorhabditis elegans

<400> SEQUENCE: 33

```
Met Ala Gln Ser Val Pro Pro Gly Asp Ile Gln Thr Gln Pro Gly Thr
1               5                   10                  15
Lys Ile Val Phe Asn Ala Pro Tyr Asp Asp Lys His Thr Tyr His Ile
            20                  25                  30
Lys Val Ile Asn Ser Ser Ala Arg Arg Ile Gly Tyr Gly Ile Lys Thr
        35                  40                  45
Thr Asn Met Lys Arg Leu Gly Val Asp Pro Pro Cys Gly Val Leu Asp
    50                  55                  60
Pro Lys Glu Ala Val Leu Leu Ala Val Ser Cys Asp Ala Phe Ala Phe
65                  70                  75                  80
Gly Gln Glu Asp Thr Asn Asn Asp Arg Ile Thr Val Glu Trp Thr Asn
                85                  90                  95
```

```
                                  -continued

Thr Pro Asp Gly Ala Ala Lys Gln Phe Arg Arg Glu Trp Phe Gln Gly
            100                 105                 110

Asp Gly Met Val Arg Arg Lys Asn Leu Pro Ile Glu Tyr Asn Pro
            115                 120                 125
```

COMPOSITIONS AND METHODS OF NEMATODE CONTROL

This application is a divisional application of U.S. Patent application Ser. No. 09/863,063 filed May 21, 2001, now abandoned, entitled "Compositions and Methods of Nematode Control" which is hereby incorporated herein by reference in its entirety, which claims the benefit of U.S. Provisional Patent Application Ser. No. 60/205,829 filed on May 19, 2000, entitled "Control of Nematodes, Stimulation of Nematode Resistance, and Screening Methods for Identifying Anti-Nematode Factors", incorporated herein by reference in its entirety, and U.S. Provisional Patent Application Ser. No. 60/274,358 filed on Mar. 08, 2001, entitled "Control of Nematodes", incorporated herein by reference in its entirety.

FIELD OF THE INVENTION

The present invention is related to compositions and methods of nematode control and, in particular, to compositions and methods for control of nematode fertility, for identifying anti-nematode agents, and potentiating host resistance.

BACKGROUND OF THE INVENTION

Parasitic nematodes infection of plants and animals are widespread with approximately 3 billion people being infected worldwide, 100 million lives lost, and an estimated $80 billion worth of crops lost annually to these organisms. Human conditions include river fever and elephantiasis each of which cause terrible human suffering. Parasitic nematodes are also a major problem in livestock, horses, and pets. Free living nematodes also damage plants during feeding, compete for oxygen, and transmit disease. Certain anti-nematode agents are commercially available. Disadvantages to these agents, such as the carbamates, include their extreme toxicity to most animals and all humankind. Other agents, such as ivermectin and its derivatives have undesirable toxic effects and potentially severe side effects especially those related to behavior and mental health. In addition, ivermectin resistant strains of nematodes develop relatively quickly and are reported in crops, livestock, and humans.

It is clear from the widespread and sever nature of the nematode problem and the adverse or toxic nature of many nematode treating agents, that more effective compounds and methods for controlling nematodes and identifying anti-nematode agents are needed.

STATUS OF THE PRIOR ART

McCarter et al, (1999) discloses that in the absence of sperm, the production of oocytes remains arrested in nematodes.

Klass, M. R., et al. (1981) discloses that major sperm protein is a structural protein in sperm cells of nematodes.

It is disclosed that all cells of Caenorhabditis elegans are directly observable in the intact Caenorhabditis elegans animal as reviewed in Hubbard and Greenstein (2000).

Video microscopy is disclosed to be used for observing the late stages of oocyte development (Ward and Carrel, 1979; Albertson, 1984; Albertson and Thomson, 1993; McCarter et al., 1997; Rose et al., 1997; Hall et al., 1999).

SUMMARY OF THE INVENTION

The present invention provides, in part, compositions and methods for controlling nematode populations, identifying anti-nematode agents, enhancing host resistance to nematode infection, and treating plants and animals for nematodes.

Although the present invention is not bound by mechanism or theory, it is related, in part, to the surprising discovery made by the inventors that the major sperm protein (MSP) of nematodes is a molecular signaling factor which stimulates maturation of the female reproductive system in nematodes. Biological activities of MSP in this regard include, but are not limited to: oocyte maturation, gonadal sheath cell contraction, and ovulation.

One advantage of the present invention is that inhibitors of the MSP signaling mechanism described herein are contemplated to be highly specific to inhibiting nematode proliferation and spread while being non-toxic to vertebrates because the MSP gene and polypeptide are highly conserved between groups and divisions within the Phylum Nematoda, including the genera and species. Vertebrates and other non-nematode organisms, on the other hand, are not known to have an MSP gene, or protein. Thus, inhibitors of MSP stimulated female sexual maturation (FSM) are expected to be specific to organisms of the Phylum Nematoda.

Another advantage of the present invention is that the high sequence conservation observed among MSP from various nematodes suggests that resistance to anti-nematode agents that target MSP is likely to be minimal as mutational changes in MSP in are likely to result in a reduction of reproductive capacity.

Still another advantage of the present invention is that, in general, MSP and FSM effective domains thereof, can be prepared in soluble form. Thus, MSP provides an easily handled target for methods of the present invention including in high-throughput assays for identification of MSP binding and FSM blocking agents.

One aspect of the present invention includes a method for identifying an anti-nematode agent by contacting a test compound to a nematode and monitoring the FSM response, wherein inhibiting test compounds are selected as anti-nematode agents.

Another aspect of the present invention includes identifying anti-nematode agents by selection of major sperm protein binding agents as many of these agents will also inhibit FSM. Screening methods are described to determine which MSP binding agents also inhibit FSM.

In a further aspect of the present invention, a reduction or an absence of MSP signal transduction impairs or virtually eliminates nematode fertility.

Still further aspects of the present invention provide methods of controlling nematode populations including, but not limited to: free living nematode populations and parasitic nematode populations which, in turn include animal and plant parasitic nematodes.

Additional aspects, embodiments, and elements of the present invention are described below, including in the detailed description of the invention, the examples, and the claims. Aspects, embodiments, and elements described herein are not meant to limit the present invention in any way including to any particular set thereof. Further aspects, embodiments, elements and equivalents thereof, will be readily apparent based upon the present disclosure and are considered to be within the spirit and scope of the present invention.

BRIEF DESCRIPTION OF THE DRAWINGS

FIG. 6A displays an alignment of a first portion of twenty-seven MSP polypeptides from C. elegans.

FIG. 6B displays an alignment of the second portion of the twenty-seven MSP polypeptides from C. elegans shown in FIG. 6A. The SEQ ID Numbers are not meant to include the N-terminal most methionine which is believed to be cleaved during processing.

FIG. 7 displays and alignment of Ascaris suum alpha and beta MSP isoforms and MSP-142 of C-elegans. Again, the SEQ ID Numbers are not meant to include to N-terminal most methionine which is believed to be cleaved during processing.

FIG. 9 shows an alignment (performed by visual inspection) of the C-termini of MSPs from wide ranging nematode species and demonstrates that there is a remarkable sequence conservation. The residues numbers relative to the full length (minus the methionine) polypeptide are 106–126 for each of the following. Ascaris suum (As) MSP isoforms alpha and beta (GenBank accession numbers P27439 and P27440) fragment from 106–126 are both represented by SEQ ID NO:13 (identical polypeptides). Onchocerca volvulus (Ov) MSP isoforms 1 and 2 (P13262 and P13263) are also represented by SEQ ID NO:13. Globodera rostochiensis (Gr, the potato cyst nematode) MSP isoforms 1, 2, and 3 are each represented by SEQ ID NO:14. C. elegans (Ce) MSP isoforms 142 and 33 (P53017 and P53019) are each represented by SEQ ID NO:15.

DETAILED DESCRIPTION OF THE INVENTION

Figure 1:
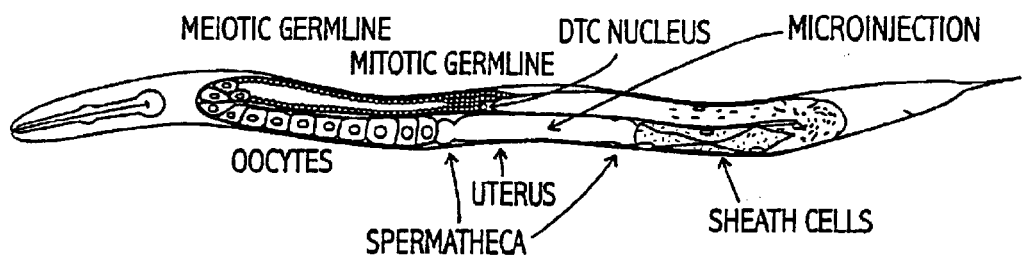
FIG. 1 shows a cross-section of a nematode and includes a depiction of the reproductive anatomy. Microinjections as described herein are preferred to be carried out at the point indicated.

Given the human suffering and economic loss due to nematodes, it is critical that effective and safe anti-nematode compounds and methods for controlling nematodes are identified. Although not bound by mechanism or theory, the present invention takes advantage of the discovery by the inventors that nematode major sperm protein regulates the fertility of nematodes. Provided herein are compositions and methods for inhibiting or blocking major sperm protein action in fertility.

Certain utilities of the compositions and methods of the present invention include, but are not limited to: identifying anti-nematode agents, manufacturing anti-nematode agents, providing reagents for screening test compounds for anti-nematode activity, controlling nematode populations, treating animals and plants for nematode infection or infestation, treating animals and plants for certain negative effects of nematodes (including environmental or other effects of free living nematodes), raising host resistance to nematode infection, and prophylactic treatments to retard nematode infection or the spread of nematodes.

1.0 Definitions

Unless otherwise defined, all technical and scientific terms used herein have the same meaning as commonly understood by one of ordinary skill in the art to which this invention pertains. In case of conflict, the present document, including definitions, will control.

Descriptions of preferred methods and compositions are provided herein, but should not be construed to be limiting.

As used herein "prophylaxis" or "prophylactic treatment" refers to measures designed to preserve health or retard the spread of disease. "Prophylaxis" or "prophylactic treatment" do not mean herein a certainty of the preservation of health or a certainty of a halt to a spread of a disease.

MSP is an abbreviation for major sperm protein.

FSM is an abbreviation for female sexual maturation.

FSM is meant to include, but is not necessarily limited to oocyte maturation, sheath cell contraction, and ovulation.

SCM is an abbreviation for sperm-conditioned media.

C. elegans is an abbreviation for the nematode genus and species Caenorhabditis elegans.

A. suum is an abbreviation for the nematode genus and species Ascaris suum.

The term "biological activity" is meant to include, but is not limited to: FSM, oocyte maturation, sheath cell contraction, and ovulation.

The term "polypeptide" is known in the art, meanings of which are included herein. However, in the event of conflict, the term "polypeptide" means herein, an amino acid polymer of two units or greater (e.g., a dipeptide or greater).

The term "polynucleotide" is known in the art, meanings of which are included herein. However, in the event of conflict, the term "polynucleotide" means a nucleic acid polymer of two units or greater (e.g., a dinucleotide or greater).

The term "isolated polypeptide" refers to a polypeptide that is at least partially removed from the milieu of molecules in which it occurs in nature.

The term "isolated polynucleotide" refers to a polynucleotide that is at least partially removed from the milieu of molecules in which it occurs in nature. As used herein, "isolated polynucleotide" also means that the polynucleotide is not identical in structure to a naturally occurring genome or fragment of a genome that spans more than three distinct, non-overlapping, genomically consecutive genes in length.

Additional definitions of specific terms and phrases are provided herein as needed.

2.0 Caenorhabditis Elegans as a Model System

Caenorhabditis elegans, or C. elegans, is a widely accepted genetic model system for studying the genes and gene functions of higher organisms. C. elegans is also a widely accepted model system for studying all features of other members of the phylum Nematoda. These features include germline development, female sexual maturation, oocyte maturation, sheath cell contraction, and ovulation (reviewed by Hubbard and Greenstein, 2000).

C. elegans is a primitive organism which nonetheless shares many of the essential biological characteristics that are central problems of, for example, human biology. The worm is conceived as a single cell which undergoes a complex process of development, starting with embryonic cleavage, proceeding through morphogenesis and growth to the adult. It has a nervous system including a rudimentary brain, exhibits behaviors, and can "learn". It produces sperm and eggs, mates and reproduces. After reproduction it gradually ages, loses vigor and finally dies. Certain genetic features of C. elegans have been extensively characterized and the genome has been sequenced. All 959 somatic cells of its transparent body are visible with a microscope, and its average life span (in the normal state) is a mere 2–3 weeks. Thus, C. elegans provides an ideal compromise between complexity and tractability.

3.0 Germline Development in Nematoda

In general, sexual reproduction of nematodes depends on coordination between meiotic cell cycle progression, gametogenesis, and fertilization. For example, gamete differentiation is coordinated with meiotic cell cycle transitions so that fertilization produces a diploid zygote capable of completing embryogenesis and growing into a fertile adult. Normally, nematode oocytes arrest during diplotene/diakinesis of meiotic prophase (after the completion of meiosis I and meiosis II) while they grow in size. The release of oocytes from this arrest occurs during meiotic maturation during which the nuclear envelope (i.e., germinal vesicle) breaks down, the cytoskeleton rearranges, and the oocyte prepares for fertilization.

Typically, the progression of germline development in C. elegans, and members of Nematoda in general, is as follows. During embryogenesis a reproducible and largely invariant cell lineage generates two germline precursor cells, Z2/Z3, and two somatic gonadal precursor cells, Z1/Z4, that together comprise the gonadal primordium at hatching (Kimble and Hirsh, 1979; Sulston et al., 1983). During post-embryonic development, Z1 and Z4 give rise to the entire somatic gonad (in the hermaphrodite, these structures are distal tip cells (DTCs), sheath cells, spermathecae, and uterus) and Z2 and Z3 give rise to the germ line. In later larval stages the germ line contains a stem-cell population that contributes cells to the meiotic pathway. Although germline nuclei reside in a syncytium at these stages, individual germline nuclei and their surrounding cytoplasm are typically referred to as a "germ cell". Development of the soma and germ line in both sexes, hermaphrodites and males, is coordinated by intercellular signaling. The self-fertile hermaphrodites are essentially modified females that produce sperm for a short time early in gametogenesis and then produce exclusively oocytes as adults. Males produce only sperm and can mate with hermaphrodites to produce cross progeny.

During post-embryonic development germ cells proliferate mitotically forming approximately 1000 nuclei in hermaphrodites and 500 in males. The C. elegans adult hermaphrodite gonad consists of two U-shaped gonad arms (FIG. 1). The two equivalent gonad arms of the adult hermaphrodite gonad have been described at an ultrastructural level (Hirsh et al., 1976; Hall et al., 1999; see FIG. 1). The distal portion of the gonad contains syncytial germline nuclei surrounded by incomplete membranes. The germ cells are connected to a core cytoplasm, also called the rachis. The stem-cell population is restricted to the distal-most part of the germ line; germ cells enter meiosis as they move proximally. In hermaphrodites, approximately the first 40 germ cells to enter meiotic prophase in each gonad arm differentiate as spermatocytes which complete meiosis to form approximately 160 sperm during the fourth larval stage of development. Upon progression to the adult stage, the germ cells differentiate as oocytes. Oocytes are surrounded by the proximal gonadal sheath cells (see FIG. 1).

The gonadal sheath cells are somatic cells that appear to play several roles important for the structure, integrity, and reproductive functions of the gonad (McCarter et al., 1997; Rose et al., 1997). The ten thin gonadal sheath cells can be subdivided into five pairs (1–5) with each pair having a distinct position along the proximal-distal axis of each gonad arm (FIG. 1). These elongated myoepithelial cells lie between germ cells and the gonadal basal lamina (Hirsh et al., 1976; Kimble and Hirsh, 1979; Strome, 1986; Hall et al., 1999). The distal sheath cells (pair 1) have an unusual cellular structure with a flattened soma pressed into the gonad such that the cytoplasm is concentrated into a series of wedges that insert between the germ cells. Pair 1 distal sheath cells also extend finger-like filopodia between distal germ cells. Pair 2 ensheathes the loop region. The proximal sheath cells (pairs 3–5; see FIG. 1) contain thick and thin filaments and contract to drive ovulation (Strome, 1986; Myers et al., 1996; McCarter et al., 1997; Rose et al., 1997; Hall et al., 1999). The proximal sheath cells are positioned in an interdigitating pattern form gap junctions with one another, and are closely apposed to oocytes (Hall et al., 1999). On their basal surfaces the proximal sheath cells attach to the gonadal basal lamina via hemi-adherens junctions which also serve to anchor the actin cytoskeleton and the contractile apparatus within the sheath cells. At their apical face, the proximal sheath cells often form gap junctions with oocytes. Yolk particles synthesized by the intestine (Kimble and Sharrock, 1983) gain access to oocytes for receptor-mediated endocytosis (Grant and Hirsh, 1999) by first moving through the sheath pores (Hall et al., 1999). The most proximal sheath cells, pair 5, directly attach to the spermatheca. The spermatheca (1 per gonad arm) is a flexible accordion-like structure connected to the gonad arm distally and to the uterus proximally. The spermatheca expands greatly to accommodate oocytes, which are fertilized as they enter from the gonad arm during ovulation.

4.0 Female Sexual Maturation

The phrase "female sexual maturation" is defined herein to include, but is not limited to: meiotic maturation, completion of the meiotic divisions, oocyte production, oocyte or ovum maturation, and the events and processes of sheath cell contraction and ovulation. In certain embodiments, "maturation" generally relates to the process by which an oocyte or an ova becomes competent for being fertilized. For example, female sexual maturation includes maturation of a female reproductive cell and maturation of an oocyte. In another example, as used herein, female sexual maturation also includes a contraction of a sheath cell which is considered herein to be a female reproductive cell. Thus certain cells of the nematode reproductive system are referred to as female reproductive cells, even though they are not an oocyte or ovum per say.

5.0 Meiotic Maturation, Ovulation, and Completion of the Meiotic Divisions

Fully grown oocytes remain in the diakinesis stage of prophase I prior to undergoing meiotic maturation, ovulation, and fertilization. The nuclear envelope of the most proximal oocyte breaks down about 5 minutes prior to ovulation as it enters meiotic M-phase from prophase (Ward and Carrel, 1979; McCarter et al., 1999). During maturation, the oocyte also undergoes a structural change termed cortical rearrangement (McCarter et al., 1999). These changes within the oocyte coincide with a reproducible sequence of somatic motor events mediated by the proximal sheath cells and the distal spermatheca resulting in ovulation. During ovulation the mature oocyte enters the spermatheca and is fertilized. The fertilized oocyte then passes into the uterus where both meiotic divisions are completed and embryogenesis begins (Albertson, 1984; Albertson and Thomson, 1993; McCarter et al., 1999). McCarter et al, (1999) discloses that in the absence of sperm, the production of oocytes remains arrested in nematodes.

6.0 Assay to Identify the Stimulator of Female Sexual Maturation

Figure 2:
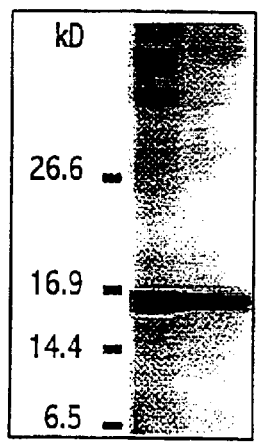
FIG. 2 shows a polyacrylamide gel electrophoresis of crude sperm-conditioned medium (SCM) (left lane) and isolated 14 kDa female sexual maturation (FSM) stimulating factor (single band in right lane) identified as major sperm protein (MSP) of C. elegans.

The present inventors developed an in vivo assay for female sexual maturation and used the assay to discover that the major sperm protein (MSP) is the particular stimulator of female sexual maturation. The general procedures used are as follows. Large quantities of sperm (>108) are purified using a modification of methods developed by Klass and Hirsh (1981). Synchronized cultures of fog-2(q71), which are 50% male and 50% female, are used to purify adult males (Lewis and Flemming, 1995). Mutations in the fog-2 gene block spermatogenesis in XX animals, transforming them into females, but have no effect on X0 animals, which are fertile males (Schedl and Kimble, 1988). Males are separated from females, larvae, and embryos based on size by sieving through NITEX screens of various pore sizes. The populations of males isolated in this way are generally >99% pure. To isolate sperm, males are placed between two PLEXIGLASS plates and smashed in a vice grip (The Home Depot, Inc.). Intact sperm are then purified from the carcasses by filtration through NITEX filters (20 micron pore size) and washed in M9 phosphate buffer (Sulston and Hodgkin, 1988) using several rounds of low speed centrifugation and resuspension. Sperm-conditioned medium (SCM) are prepared by incubating purified sperm in M9 for different periods of time (e.g., 1–12 hours) and removing the sperm by centrifugation and filtration through a 0.2 micron filter. Microscopic analysis suggests that the sperm are not lysing during the incubation. Polyacrylamide gel electrophoresis (PAGE) also indicates that the sperm are not lysing during the incubation and also reveals that that an approximately 14 kDa protein is enriched in SCM. Referring to FIG. 2, an single protein band at approximately 14 kDa is apparent in the second lane. PAGE results for unfractionated SCM are displayed in lane 1.

Another aspect of the present invention provides an assay to screen SCM for maturation- and contraction-inducing activities, comprising microinjecting SCM into the uterus of reduced capacity sperm producing female nematodes (virgin fog-2(q71) females are used in certain preferred embodiments). Maturation and sheath cell contraction are monitored by time-lapse video microscopy (see Rose et al. (1997) for a general description of time-lapse video microscopy of nematodes). Dramatic increases in oocyte maturation and sheath cell contraction rates are observed following injection of SCM. By contrast, no activity, or essentially no activity, is observed following injection of female extracts, 1-methyladenine, acetylcholine, oxytocin, or M9 buffer. The above described embodiment, provides a bioassay for sperm derived factors that promote oocyte maturation and sheath cell contraction. It is disclosed in the present invention that the activity is, at least in part, soluble and present in the sperm-conditioned media. This suggests that the factor is secreted by the sperm. Thus, it is a discovery of the present invention that while the sperm are sometime physically blocked by the valve, a soluble (diffusible) factor is secreted from the sperm to affect FSM and this factor penetrates the valve.

Figure 3:
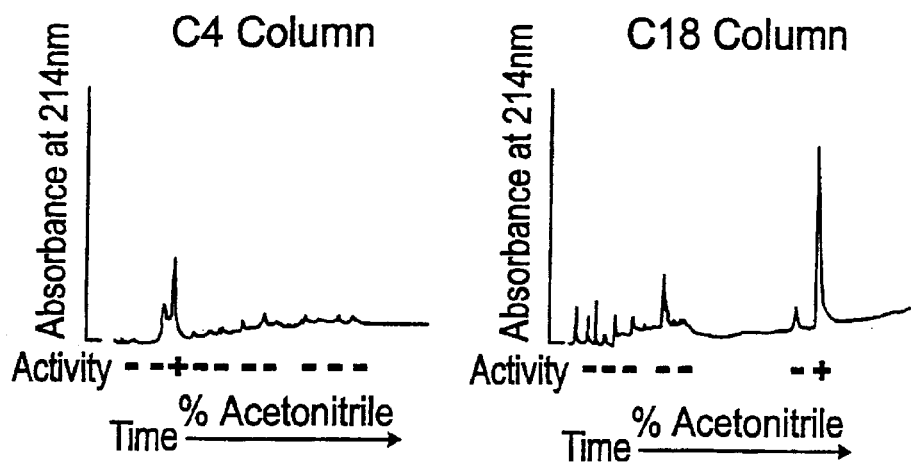
FIG. 3 shows HPLC traces of fractionation of SCM on C-4 and C-18 columns. The "+" sign indicates the respective fractions with FSM positive biological activity.
Figure 4:
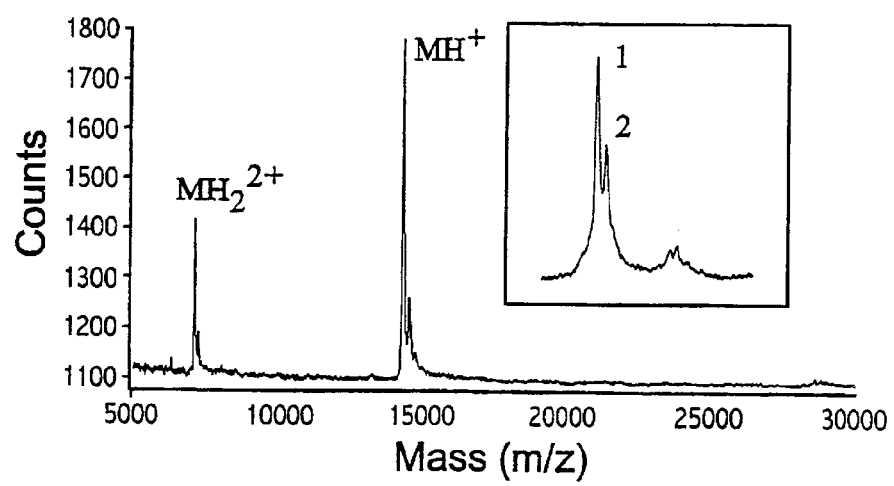
FIG. 4 shows mass spectra of the FSM positive fractions from the HPLC purification. The mass spectra confirm MSP-3 and MSP-142 of C. elegans are present in the biologically active SCM. No other factors were observed or identified in these mass spectra.

Still another aspect of the present invention provides compositions and methods for fractionation of SCM, and other nematode biological materials, for isolation of the FSM stimulatory factor. In one example, fractionation is performed using reversed phase high pressure liquid chromatography (HPLC) on Vydak C-4 and C-18 analytical columns. FIG. 3, a fraction marked by a + sign is the only active fraction recovered when the SCM is fractionated on the C-4 and C-18 columns, respectively (as determined using the in vivo FSM assay described herein). The biologically active fraction is analyzed using MALDI mass spectrometry peptide mapping and sequencing, identification techniques which are known in the art (FIG. 4). This result is verified by producing MSP-38 (GenBank Ac. # CAA93089) and MSP-142 (GenBank Ac. # CAB03037) in bacteria and purifying the respective isoforms using a commercially available 6-His tagging and protein product purification system. The inserts are cloned into the pQE-30 Type IV Kit available from Qiagen. The vector includes the 6-His tagging system and methods for this cloning and use of the 6-His tagging system of identification and purification of expressed polypeptides are well known. The result is also confirmed using C. elegans MSP-77. Additional tests by MADLI-MS analysis demonstrate the C. elegans MSP in SCM is MSP-3 and MSP 142 (Miller et al., 2001).

Figure 5:
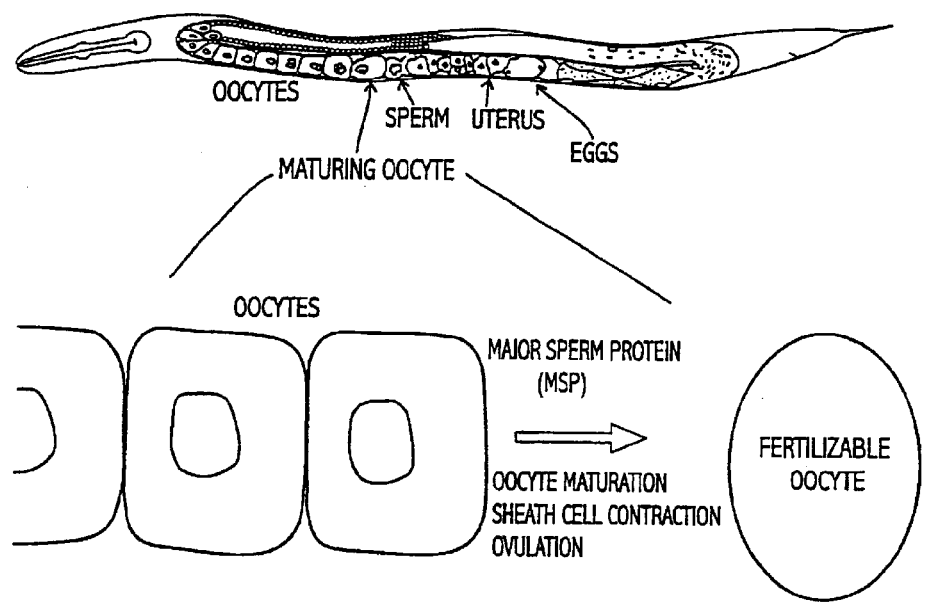
FIG. 5 is a diagram of MSP mediated cellular communication between female reproductive cell (for example, the oocytes) and sperm.

Microinjection of purified recombinant MSP mimics the biological response (FSM) seen using the active, fraction purified from SCM. Additionally, the recombinantly produced protein yields the same peptide map as the MSP from the active SCM fraction when cleaved with trypsin and analyzed using mass spectrometry. These results demonstrate that C. elegans sperm secrete, or otherwise release, the major sperm protein, that the MSP signal is at least partially soluble in the extracellular fluid surrounds the sperm and in buffers, and that MSP dramatically increases FSM (including oocyte maturation, sheath cell contraction, and ovulation rates). The concept of MSP directed signal transduction of FSM including oocyte maturation, sheath cell contraction, and ovulation is diagrammed in FIG. 5. Referring to FIG. 5, MSP serves as a simple molecule for communication between the sperm and non-mature or arrested oocytes and inactive female reproductive cells that sperm is present and ready to fertilize the egg.

Furthermore, the MSP is believed to be necessary and sufficient for stimulating that communication or signal transduction of FSM. While it is contemplated and other factors may form a web-like network of upstream and/or downstream signal cascade, it is an advantage in certain embodiments herein that the role of MSP is quite uncomplicated. Thus, MSP provides an excellent target for anti-nematode agents. Also, due to the high sequence conservation between MSP polypeptides in all known nematodes, it is contemplated that nematodes will not readily evolve resistance to compounds or agents that target MSP.

7.0 MSP is Known as a Structural Protein Localized Within the Sperm Cell

MSP is known in the art as a structural protein of the nematode sperm (Klass, M. R., et al., 1981). Thus, it is a surprising discovery of the present invention that MSP is also a nematode female sexual maturation factor (stimulator, signal transduction element, etc.).

It is widely accepted that motility of nematode sperm is not actin based, but rather is dependent upon MSP structure and function. Inside the sperm cell, dimeric MSP assembles at one end of a fibrous polymer of dimeric MSP and disassembles at the other end in a treadmill-like fashion which enables the sperm to protrude and withdraw pseudopodia related to motility.

8.0 Sequence Conservation Among the Many MSP Sequences Described

There are likely more than sixty copies of the MSP gene in the *C. elegans* genome and it is believed that most of these MSP genes are transcribed. Referring to FIGS. 6A and 6B, twenty-seven MSP polypeptide sequences are provided corresponding to polypeptides transcribed from apparently distinct MSP genes or polynucleotide sequences. Certain other nematodes apparently have fewer copies of MSP. For example, *A. suum* are believed to have two copies of an MSP gene both of which are believed to be transcribed into polypeptides.

Twenty-seven polypeptide sequences for FIGS. 6A and 6B are aligned using Divide-and-Conquer Multiple Sequence Alignment which is currently available over the world wide web (www) at the URL http://bibiserv.techfak.uni-bielefeld.de/dca/. The server is located at the Practical Computer Science and Bioinformatics research group which is run by Robert Giegerich. The physical location is: Robert Giegerich, AG Praktische Informatik, Technische Fakultät, Universität Bielefeld, Postfach 10 01 31, D-33501 Bielefeld, Germany. The parameters used are Blosum 62 predefined substitution matrix, free shift activated, approximate cut positions activated, recursion stop size L set to 20, window size W set to 0, and weight intensity lambda set to 0. The algorithm and method are disclosed in Stoye (1998).

Referring to FIGS. 6A and 6B, it is known that the N-terminal most methionine (from the ATG translation start site) is cleaved. It is expected that both forms (with and without the methionine) of MSP polypeptides are active in FSM; therefore, the methionine was included in FIG. 6A. However, the references to the SEQ ID Numbers provided in FIG. 6B correspond to MSP polypeptide sequences of 126 amino acids and are without each N-terminal most methionine as shown in FIG. 6A.

Again, referring to FIGS. 6A and 6B, the sequences of the numerous *C. elegans* MSP display a high degree of sequence homology. Very few sequence variations are observed. Residues that vary from the global (general) consensus within a column (determined visually) are marked in bold letter and underlined in FIGS. 6A and 6B. Because MSP polypeptide sequences, and even those of the most divergent known nematodes (see below), are so highly conserved; the preferred method for alignment is by visual inspection. For example, two or more MSP polypeptide sequences can be easily lined up next to one another on a computer screen or as written out on a paper and one moved against another until the majority of the bases match. Percent identity between any two sequences is calculated by counting the number of residues that do not match, dividing by the total number of residues in the total sequence being compared (or the shortest of the sequences being compared if one of the pair is shorter in length), multiplying by 100, and expressing the resulting value as a percent.

Using this approach, one of ordinary skill in the art can easily determine an alignment of a given MSP isolated from any member of the phylum Nematoda to another MSP, including to a *C. elegans* MSP, and in preferred embodiments the MSP specified in SEQ ID NO:2. It is also preferred that the alignment selected is the one which produces the highest sequence identity as described above.

Thus, for example, the visual inspection method described above is used to align the sequences for the two known MSPs from *A. suum* (alpha and beta) with MSP-142 of *C. elegans* (see FIG. 7). Again, very little sequence variation is observed between MSP polypeptides from these nematodes that are separated by hundreds of millions of years of evolutionary pressure. This indicates that the structure function relationship in MSP is tight and sequence variation likely results in a reduced fitness of the organism.

9.0 Biological Activities of MSP on FSM are Conserved in Phylum Nematoda

*Ascaris suum* is believed to be one of the most widely separated nematode species from *C. elegans* in terms of both evolution (hundreds of millions of years post divergence from the common organism) and in terms of distinctness of the MSP sequence including at the polypeptide level. For example, evaluation of the biological activity of isolated MSP alpha and MSP beta from *A. suum* in the in vivo FSM assay described above serves as a model system for demonstrating that MSP sequences in general stimulate nematode FSM in all or nearly all member of the phylum Nematoda.

MSP, isoforms alpha from *A. suum* is isolated from *A. suum* nematodes or the corresponding nucleotide is cloned and expressed in bacteria, for example. The specific sequence used is Accession Number P27439 in the NCBI database (maqsvppgdintqpsqkivfnapyddkhtyhikitnaggrrigwaikttn mrrlsvdppcgvldpkekvlmavscdtfnaatedlnndritiewtntpdga akqfrrewfqgdgmvrrknlpieynl) and is set forth in SEQ ID NO: 11, wherein SEQ ID NO:11 does not include the N-terminal methionine in order to represent the polypeptide that is believed to be cleaved during cellular processing (see FIG. 7).

MSP, isoforms beta from *A. suum* is isolated from *A. suum* nematodes or the corresponding nucleotide is cloned and expressed in bacteria, for example. The specific sequence used is Accession Number P27440 (maqsvppgdintqpgskivfnapyddkhtyhikitnaggrrigwaiktt nmrrlgvdppcgvldpkesvlmavscdtfnaatedlnndritiewtntpdga akqfrrewfqgdgmvrrknlpieynl) in the NCBI database and is set forth in SEQ ID NO: 12, wherein SEQ ID NO:12 does not include the N-terminal methionine in order to represent the polypeptide that is believed to be cleaved during cellular processing.

Microinjection of MSP, isoform alpha or MSP, isoform beta into the sperm defective (or reduced sperm capacity) female *C. elegans* as described above results in a restoration of apparently normal FSM biological activity even though no sperm are added. This provides support for using any combination of MSP polypeptide including as expressed from MSP polynucleotides. Methods known in the art for expressing polynucleotides that are preferred herein include, but are not limited to: expression in bacteria, transient expression in nematodes, stable expression in nematodes, and transgenic expression in nematodes. Transgenic expression in nematodes includes gonadal specific expression and ectopic expression, such as in transgenic expression in somatic cells of the nematode.

10.0 Experiments Demonstrating that MSP Stimulates FSM

The biological activities of MSP-77 and MSP 38 are studied using the in vivo FSM assays described herein.

Figure 8:
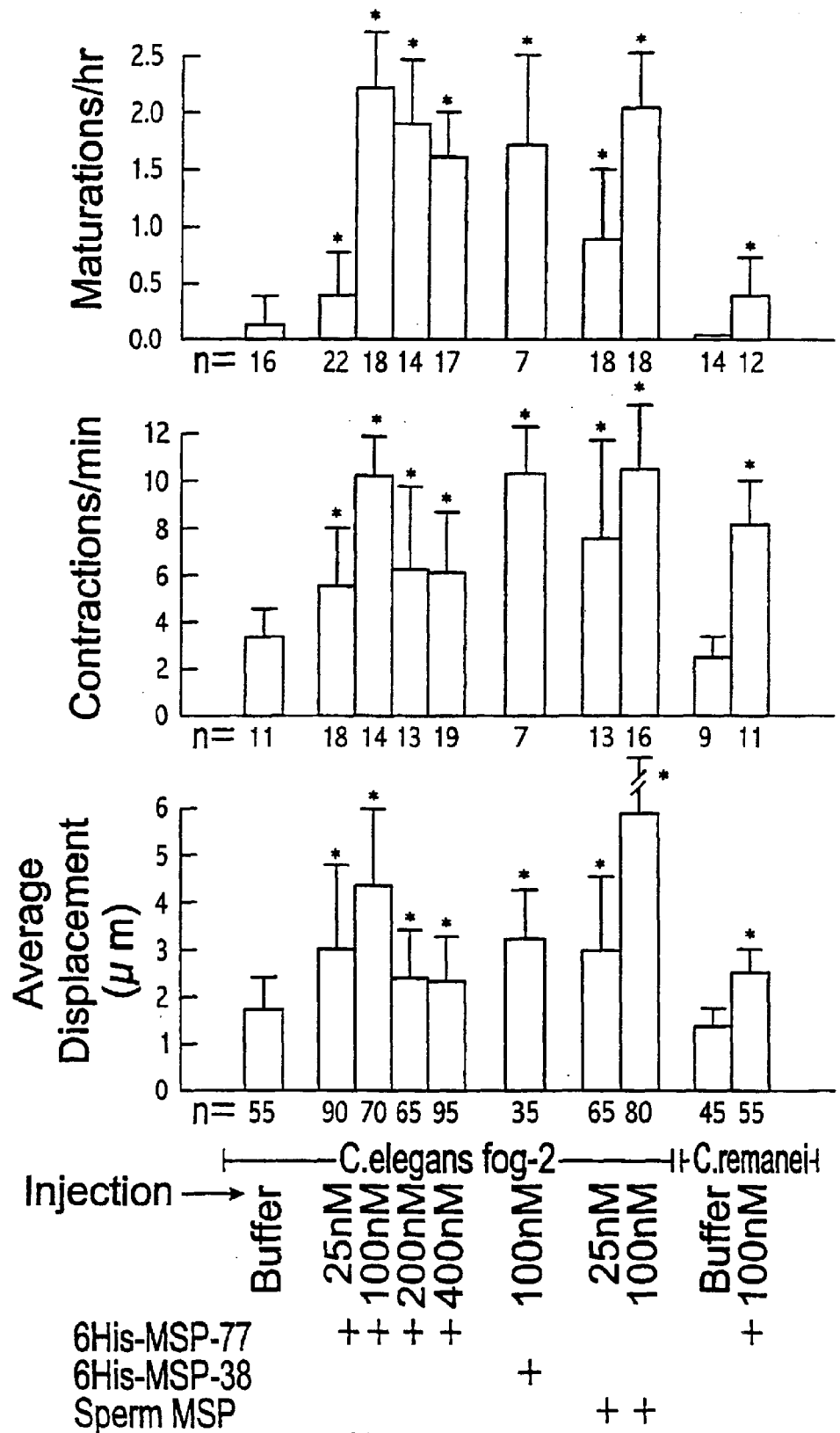
FIG. 8 is a bar graph demonstrating bioactive properties of MSP-77 and MSP-38, and sperm protein (versus and buffer control) in stimulating FSM in nematodes. The top panel displays maturations per hour which is a biological measure of oocyte maturation. The center panel displays contractions per minute which is a biological measure of sheath cell contraction. The bottom panel displays average displacement (in microns) which is another measure of sheath cell contraction. Measurements are made for buffer and the shown concentrations of MSP-77, MSP-38, and sperm MSP. The 6His marking denotes that the MSP includes a histidine tag (Qiagen) and was purified using this system.

Referring to FIG. 8, MSP isolated from male nematodes, as well as MSP produced in bacteria stimulate oocyte maturation and sheath cell contraction when introduced into female nematodes with reduced sperm formation such as fog-2 mutants (MSP-77 and MSP-38, in this figure, are isolated from the bacteria with a 6His tag. This general protein isolation technique is known in the art). Again, referring to FIG. 8, the top panel displays maturations per hour which is a biological measure of oocyte maturation. The center panel displays contractions per minute which is a biological measure of sheath cell contraction. The bottom panel displays average displacement (in microns) which is another measure of sheath cell contraction. Measurements are made for buffer and the shown concentrations of MSP-77, MSP-38, and sperm MSP. The 6His marking denotes that the MSP includes a histidine tag (Qiagen) and was purified using this system.

Similar experiments are performed with MSP-3 and MSP-142 (which are identified herein to be localized in sperm-conditioned medium), and MSP from *C. briggsae* and *C. remanei*. Also, experiments are performed with MSP from the distantly related *A. suum*. Each experiment demonstrates that MSP is essentially interchangeable with regard to its biological activities in FSM.

11.0 The Carboxyl-Terminus of MSP Shows High Sequence Conservation

Residues 105 through 125 of MSPs derived from nine different genera of nematodes show a 100% sequence identity in these 19 consecutive amino acid residues (see FIG. 9). These nematodes represent free-living (*C. elegans*), animal parasites (*Ascaris* and *Onchocerca*), and plant parasites (*Globodera*). (Specifying these genera as free-living, animal parasites, or plant parasites is not meant to limit the range that Nematodes inhabit the environment. In general many groups of nematodes have a diverse range).

12.0 Certain Domains Within MSP Differentially Stimulate FSM Activities

Figure 10:
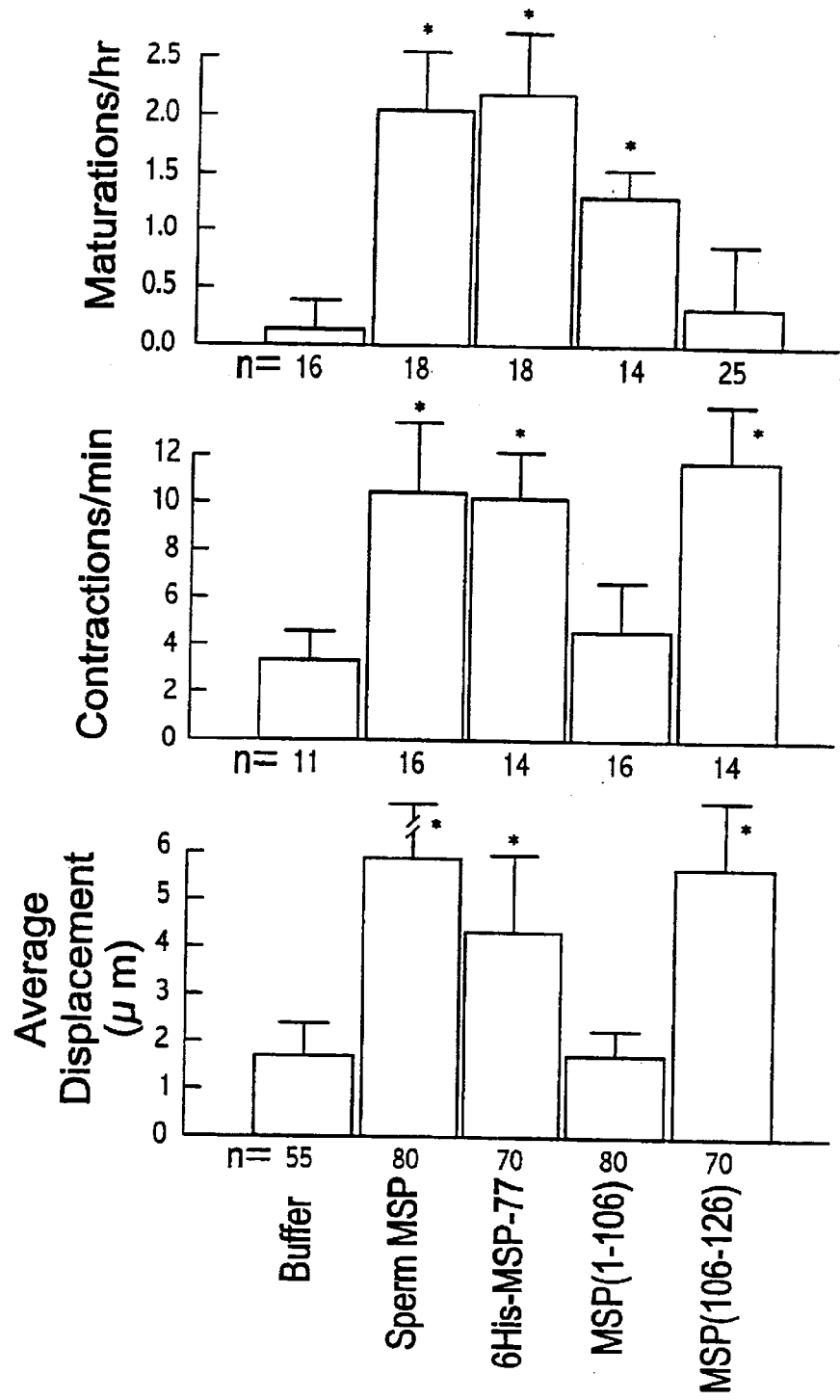
FIG. 10 is a bar graph showing that the N-terminal region of MSP is necessary and sufficient for stimulation of oocyte maturation and the C-terminal region is necessary and sufficient for stimulation of sheath cell contraction. The N-terminal residues 1–106 (SEQ ID NO: 16) of MSP-77 (SEQ ID NO:9) are necessary and sufficient for stimulation of oocyte maturation (top panel). The C-terminal residues 106–126 (SEQ ID NO:17) of MSP-77 (SEQ ID NO:9) are necessary and sufficient for stimulation of sheath cell contraction (middle panel) and displacement (bottom panel).

Another aspect of the present invention provides that certain domains within MSP differentially regulate certain FSM activities. For example, FIG. 10 demonstrates that residues 1–106 (SEQ ID NO:16 ) of MSP-77 (SEQ ID NO:9) preferentially stimulates oocyte maturation, while residues 106–126 (SEQ ID NO:17) of MSP-77 (SEQ ID NO:9) preferentially stimulates the rate of sheath cell contraction and displacement.

Thus, the biological activities of FSM, including oocyte maturation and sheath cell contraction, can be separated and the present invention discloses that different domains within MSP are capable of regulating those activities independently.

13.0 Description of MSP Sequence Fragments

Still another aspect of the present invention includes compositions and methods for identifying and using domains within MSP including for differential regulation of the biological activities of FSM. For example, specific sized segments of MSP polypeptide are systematically screened for the impact of that domain on FSM. This provides a fine resolution map of the MSP polypeptide with regard to FSM function that can be exploited to identify and manufacture highly specific anti-nematode agents, for example. This is also useful, for example, to identify FSM related domains of particularly high sequence conservation among members of Nematoda and/or to avoid areas that might include a short region that is similar to a gene or polypeptide in another organism, the targeting of which with anti-organism agents is not desired.

In certain embodiments antibodies (polyclonal and/or monoclonal) are generated against each fragment for use in labeling, identification, and an assay of the present invention. In preferred embodiments, the antibodies are raised against those segments of MSP that influence FSM (either positively or negatively). In other embodiments, the antibodies are raised by injection of the MSP, or the FSM active domain of the MSP, into an animal (in certain embodiments, a non-human animal) using techniques known to one of skill in the art for producing antibodies. In other embodiments, the antibodies and preferably monoclonal antibodies are produced in cell, such as hybridomas or by recombinant techniques that are known in the art. In certain embodiments, the antibodies are produced in humanized form. This can be accomplished in certain embodiments by injection of the immunogenic fragment of MSP into a human.

14.0 Production of MSP Polypeptide Fragments

Segments of MSP polypeptide sequences are readily manufactured by chemical synthesis, for example by solid phase polypeptide manufacture. Alternatively, such segments can be cloned, synthesized in a heterologous cell system, and isolated. Chemical synthesis is preferred for embodiments wherein the polypeptide is a polymer of 50 residues or fewer. Segments are polypeptides that are generally 10 amino acids or more in length (referring to consecutive amino acids in an MSP sequence in this section entitled Production of MSP Polypeptide Fragments). Although, in certain embodiments useful segments are contemplated that include fewer than 10 consecutive MSP amino acids. It is believed herein that all or nearly all MSPs are essentially interchangeable with each other in regard to FSM activity. Although differences may be identified when examining the differential regulation of FSM activity.

Segments do not include the full length MSP polypeptide sequence. For example, the 126 consecutive amino acids of SEQ ID NO:2 is not a segment. Segments of a 126 amino acid MSP include 125 or fewer of consecutive amino acids of the MSP. It is preferred that the segment includes 120 or fewer, 110 or fewer, 106 or fewer, 105 or fewer, 100 or fewer, 95 or fewer, 90 or fewer, 85 or fewer, 80 or fewer, 75 or fewer, 70 or fewer, 65 or fewer, 60 or fewer, 55 or fewer, 50 or fewer, 45 or fewer, 40 or fewer, 30 or fewer, 25 or fewer, 20 or fewer, 19 or fewer, 18 or fewer, 17 or fewer, 16 or fewer, 15 or fewer, 14 or fewer, 13 or fewer, 12 or fewer, 11 or fewer, or 10 or fewer consecutive amino acids of an MSP. An MSP alignment variant means that amino acids may be substituted in any given MSP or MSP segment to make that position identical to the same position in another MSP molecule including from diverse groups of Nematoda. The segments may also be MSP alignment variant which may be referred to herein as MSP alignment variant segments. Functionally equivalent sequences and biological functional equivalents are also generally considered to be within the spirit and scope of the present invention and are described below.

Ranges of segments are also provided in certain embodiments of the present invention. For example, a 10 amino acid segment may be selected from any portion of the MSP polypeptide. An 11 amino acid segment may be selected from any portion of the MSP polypeptide. Segments of lengths including 9 amino acids (consecutive in an MSP), 10, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 55, 60, 65, 70, 75, 80, 85, 90, 95, 100, 105, 106, 110, 115, 116, 117, 118, 119, 120, 121, 122, 123, and 124 are contemplated for certain embodiments.

These segments are generally screened for FSM activity or used in assays to identify MSP binding agents (e.g., agents that bind to specific domains) and to identify anti-nematode agents. Although many segments are described, they can be screened readily for FSM activity given the present disclosure and without undue burden. A preferred method of screening is to utility high-throughput assays such as in microtitre plates or other multiple-sample format to rapidly examine a large number of segments. Such general assay are known in the art and are provided herein with regard to MSP and the embodiments of the present invention.

15.0 Description of Certain MSP Sequences

Numerous examples of MSP sequences (including polynucleotide and polypeptide) are known in the art and are useful for various embodiments of the present invention. Also, additional MSP sequences including from additional nematodes types and species can be readily determined, without burden, using conventional cloning techniques and the fact that many sequences are described. Thus, for example, primers can be designed to pull out additional polynucleotides from a pool, such as a gene or genomic library, including by PCR amplification. These polynucleotide can be expressed using standard cloning techniques and the MSP activity of the resulting polypeptide is measurable based upon the assays disclosed herein. Certain known and described MSPs are provided by way of example in Table 1 below. The MSPs are represented by Accession Numbers corresponding to files in the publicly available database maintained by the National Center for Biotechnology Information (the NCBI database). These files include polynucleotide sequences and polypeptide sequences of MSP. All information within each file identified by Accession Number is hereby incorporated herein by reference.

The NCBI database is available on the world wide web at URL "http://www.ncbi.nlm.nih.gov/" and is physically located at: National Center for Biotechnology Information; National Library of Medicine; Building 38A, Room 8N805; Bethesda, Md. 20894.

TABLE 1

| Nematode Identifier | Nucleotide Accession Numbers | Protein Accession Numbers |
|---|---|---|
| Mansonella ozzardi | AJ404225 | CAC20724 |
| | AJ404224 | CAC20723 |
| | AJ404223 | CAC20722 |
| | AJ404222 | CAC20721 |
| | AJ404221 | CAC20720 |
| | AJ404220 | CAC20719 |
| | AJ404219 | CAC20718 |
| | AJ404218 | CAC20717 |
| | AJ404217 | CAC20716 |
| | AJ404216 | CAC20715 |
| | AJ404215 | CAC20714 |
| | AJ404214 | CAC20713 |
| | AJ404213 | CAC20712 |
| | AJ404212 | CAC20711 |
| | AJ404211 | CAC20710 |
| | AJ404210 | CAC20709 |
| | AJ404209 | CAC20708 |
| | | CAC20742 |
| Onchocerca volvulus | AJ404208 | CAC20741 |
| | AJ404207 | CAC20740 |
| | AJ404206 | CAC20739 |
| | AJ404205 | CAC20738 |
| | AJ404204 | B45528 |
| | J04663 | A45528 |
| | J04662 | |
| Ascaris suum | X94249 | A45944 |
| | | P27439 |
| | | P27440 |

TABLE 1-continued

| Nematode Identifier | Nucleotide Accession Numbers | Protein Accession Numbers |
|---|---|---|
| | | AAB23264 |
| | | CAA63933 |
| Ascaris lumbricoides | M15680 | AAA29375 |
| Globodera rostochiensis | L24501 | AAA29148 |
| | L24500 | AAA29147 |
| | L24499 | AAA29146 |
| Pratylenchus penetrans | | AAB02264 |
| | | AAB02263 |
| | | AAB02262 |
| | | AAB02251 |
| | | AAB02250 |
| | | AAB02249 |
| Pratylenchus scribneri | | AAB02242 |
| | | AAB02241 |
| | | AAB02240 |
| | | AAB02239 |

16.0 An Assay for Female Sexual Maturation

A method is provided of identifying an anti-nematode agent, by contacting a test compound to a nematode and monitoring a female sexual maturation of the nematode, wherein inhibition of the female sexual maturation indicates that the test compound includes the anti-nematode agent.

The in vivo bioassay is useful, for example, to identify sperm-related factors that promote oocyte maturation and gonadal sheath cell contraction. The assay is also useful, as another example, for identifying agents that inhibit nematode female sexual maturation.

In certain embodiments of the assay, mutant nematodes are utilized which have a reduced capacity for sperm production, or lack the capacity altogether. Such mutants are disclosed to have either low rates of oocyte maturation and sheath cell contraction activity or none at all. The present invention provides compositions and methods for using these mutants to screen for factors that stimulate or inhibit female sexual maturation. In similar embodiments, compositions and methods are provided that for using transgenic nematodes. These embodiments are described in detail below.

Test compounds include any compound in general. Preferred test compounds are soluble in aqueous solution and thus conducive to typical biological assay conditions. In certain embodiments, test compounds are selected from any chemical in a library, for example, as maintained by a pharmaceutical or other company. In certain embodiments, test compounds, include proteins, glycoproteins, polypeptides, glycopeptides, amino acids, nucleic acids of any variety, including DNA, RNA, peptide nucleic acid (PNA), carbohydrates, fatty acids, lipids, etc. In certain embodiments the test compound includes any biologically active molecule.

Test compounds are administered to nematodes by any desirable method for determining which of the test compounds has an inhibitory activity on nematode fertility, female sexual maturation, or other activity described herein. For example, the test compound can be microinjected, co-injected, incubated, or fed to the nematodes. The assay measures the ability of specific test compounds to inhibit MSP stimulation of oocyte maturation, gonadal sheath cell contraction, and ovulation using optical monitoring. In addition to ovulation, laying or releasing of oocytes or embryos from the organism can be monitored optically and used as an endpoint of test compound activity. The optical monitoring can be enhanced using labeling reagents, such as fluorescent, radioactive, or enzymatic labels. These labels can be attached using standard chemistry known in the art to the test compound, a sperm, a major sperm protein, the oocyte, a sheath cell, etc.

Methods for monitoring the FSM by video microscopy are disclosed herein. Other methods for monitoring the FSM can include by radiolabel assay, fluorescent assay, etc. (Miller et al., Science 2001).

Inhibition of FSM generally refers to a reduction or termination in rate of an FSM event, in certain preferred embodiments. In other embodiments, inhibition means reduction in reproductive success, fecundity, etc. In other preferred embodiments, inhibition results in control of a population of nematodes including a free-living, parasitic, terrestrial, or an aquatic nematodes population.

17.0 Assay for Identifying Inhibitors of MSP Signaling

As described herein, an object of the present invention is to provide assays for screening test compounds to identify anti-nematode agents. In certain embodiments, the agents will be inhibitors of female nematode fertility. In certain embodiments, the agents will be inhibitors of an MSP signal transduction. Such agents generally interfere with nematode fertility and are useful as agents for control of nematodes including free-living and animal and plant parasitic nematodes. Certain embodiments of screening assays for inhibitors of MSP signal transduction follow.

18.0 Mutant Nematode Strains

In general, MSP protein is administered to a mutant hermaphrodite or female nematode strain that does not produce sperm (e.g., mutants in fog-1, fog-2, fog-3, fem-1, fem-2, fem-3, or gld-1(Fog). The MSP protein can be administered, for example, by microinjection into the uterus of the mutant hermaphrodite or female nematode strain. Such strains are available from the C. elegans Genetic Center or natural isolates of gonochoristic species. In embodiments that use microinjection, the technique is carried out according to standard practice (e.g., see LaMunyon and Ward, Genetics (1994) 138:689–692, incorporated herein by reference). Female nematode sexual maturation, such as oocyte maturation, sheath cell contraction, and ovulation are generally observed optically. Certain methods are described by McCarter et al., supra.

19.0 Wild-Type Nematode Strains

In general, methods for screening test compounds for identifying factors that inhibit nematode fertility, and preferably that inhibit female sexual maturation, can be administered to wild-type nematodes and the effect of the test compounds is usually monitored optically. Typically, the test compounds can be co-injected, incubated, or fed to nematodes. Ordinarily the endpoint of the assay measures the ability of compounds to inhibit MSP stimulation of oocyte maturation, gonadal sheath cell contraction, and ovulation as described above.

20.0 Transgenic Nematode Strains

Nematode strains that ectopically express MSP (including in non-spermatogenic tissues) can be used in methods for screening test factors to identify anti-nematode agents. Transgenic nematodes expressing MSP are generated using standard methods (e.g., Methods in Cell Biology, ed. H. Epstein and D. Shakes, San Diego Academic Press, 452–482, incorporated by reference). Inhibitor compounds are, for example, incubated with or fed to the transgenic nematodes. The assay measures the ability of compounds to inhibit nematode fertility including, but not limited to: MSP stimulation of oocyte maturation, gonadal sheath cell contraction, and ovulation as described above. Typically, the inhibition of nematode fertility is measured optically. Test factors that inhibit MSP signal transduction will inhibit the nematode female sexual maturation. In addition, most transgenic strains produce different amounts of the transgenic factor, as is known in the art. Thus, nematodes that transgenically express varying amounts of MSP can be utilized to determine anti-nematode agent concentrations that are optimized for use on a particular nematode given that different nematodes express varying levels of MSP in the wild.

21.0 MSP Binding Assay

Compounds are screened for MSP binding affinity. Panels of candidate molecules are affixed to a matrix, for example microtitre wells, using standard methods. Labeled MSP protein, such as fluorescently, radioactively, or enzymatically linked MSP protein, is incubated with the compounds attached to the matrix, and then washed off (under conditions that remove unbound labeled MSP protein). Compounds which bind MSP are recognized by retention of the label (for example, optical recognition). Alternatively, MSP protein is affixed to a matrix, for example microtitre wells, and incubated with labeled test compounds, such as fluorescently, radioactively, or enzymatically linked compounds, and then washed off, (under conditions that remove unbound labeled compound). Compounds which bind MSP are recognized by retention of the label.

In certain embodiments, compounds which bind MSP are then tested for the ability to block MSP signaling, for example by using bio-assays described herein. Compounds that inhibit or block nematode reproduction or fertility are anti-nematode agents. In certain embodiments, the anti-nematode agents are used to treat parasitic nematode infections in plants and animals by administering a therapeutically effective amount of the anti-nematode agent to the plant or animal to inhibit, or in certain cases to virtually block, nematode reproduction in the infected plant or animal.

22.0 Regulation of MSP Protein to Protein Interactions

Compounds are screened for the ability to regulate protein to protein interactions of MSP. For example, MSP is known to exist in monomeric and dimeric forms. Thus, test compounds are screened in biological assays to identify factors that prevent dimerization, multimerization (complexes with two or more MSP subunits), and for factors that prevent multimers from dissociating into monomers. The effect test compounds on multimer formation can be determined by incubating the test compound with the MSP under multimer associating and dissociating conditions. These samples can be tested for biological activity in regard to nematode fertility as described herein. Multimer and monomer formation and dissociation can be monitored by techniques known in the art. For example, SDS versus native gel electrophoresis (polyacrylamide gel electrophoresis), electrospray mass spectroscopy, and gel exclusion.

In certain embodiments, compounds which regulate multimerization of MSP (formation and dissociation of multimers/monomers) are then tested for the ability to block MSP signaling. For example by using biological assays measuring nematode female sexual maturation as described herein. Compounds that inhibit nematode reproduction are anti-nematode agents. In certain embodiments, the anti-nematode agents are used to treat parasitic nematode infections in plants and animals by administering a therapeutically effective amount of the anti-nematode agent to the plant or animal to inhibit, or in certain cases to virtually block, nematode reproduction in the infected plant or animal.

23.0 Certain Nematode Varieties

Nematoda includes the roundworms and threadworms, and comprises a phylum of generally smooth-skinned, unsegmented worms with a long cylindrical body shape tapered at the ends; the phylum includes free-living and parasitic forms both aquatic and terrestrial (adapted from Academic Press Dictionary of Science and Technology).

Table 2, below, provides a listing of the common name and scientific name of a multitude of nematode varieties. MSP genes and proteins can be derived from these or other nematode varieties and strains for use in conjunction with the present invention (e.g., in a screening assay). Also, parasitic nematode infections of these or other types of nematodes may be treated by anti-nematode agents described herein or identified as described herein. This list is not meant to be limited on the scope of the invention, but merely to be exemplary of types of nematode. Animal parasitic nematodes are also described in supplementary materials appended to this provisional application.

TABLE 2

| Common Name | Nematode Genus and species |
|---|---|
| African spiral nematode | Helicotylenchus africanus |
| Alfalfa root nematode | Heterodera goettingiana |
| Almond cyst nematode | Heterodera amygdali |
| Amaranth cyst nematode | Cactodera amaranthi |
| American dagger nematode | Xiphinema americanum |
| Amu-Darya nematode | Heterodera oxiana |
| Apple cyst nematode | Globodera mali |
| Apple root-knot nematode | Meloidogyne mali |
| Awl nematodes | Dolichodorus spp. |
| Banana meadow nematode | Pratylenchus coffeae |
| Banana nematode | Pratylenchus musicola |
| Banana root-lesion nematode | Pratylenchus coffeae |
| Banana spiral nematode | Helicotylenchus multicinctus |
| Banana-root nematode | Radopholus similis |
| Barley cyst nematode | Heterodera hordecalis |
| Barley root-knot nematode | Meloidogyne nassi |
| Beachgrass root-knot nematode | Meloidogyne sasseri |
| Beer nematode | Panagrellus silusiae |
| Beet nematode | Heterodera schachtii |
| Beet stem nematode | Ditylenchus dipsaci |
| Begonia leaf nematode | Aphelenchoides fragariae |
| Bentgrass nematode | Anguina agrostis |
| Bermudagrass cyst nematode | Heterodera cardiolata |
| Birch cyst nematode | Cactodera betulae |
| Black currant nematode | Aphelenchoides ritzemabosi |
| Blueberry root-knot nematode | Meloidogyne carolinensis |
| Boxwood spiral nematode | Rotylenchus buxophilus |
| Brassica root eelworm | Heterodera cruciferae |
| Brassica root nematode | Heterodera cruciferae |
| Brazilian root-knot nematode | Meloidogyne exigua |
| Brazilian root-knot nematode | Meloidogyne inornata |
| British root-knot nematode | Meloidogyne artiellia |
| British spiral nematode | Scutellonema brachyurum |
| Buckwheat cyst nematode | Heterodera graduni |
| Bud and leaf nematodes | Aphelenchoides spp. |
| Bud and stem nematode | Ditylenchus dipsaci |
| Bulb and stem nematodes | Ditylenchus spp. |
| Bulb nematode | Ditylenchus dipsaci |
| Bulb or stem nematodes | Ditylenchus spp. |
| Burrowing nematode | Radopholus similis |
| Burrowing nematodes | Radopholus spp. |
| Cabbage cyst nematode | Heterodera cruciferae |
| Cabbage nematode | Heterodera cruciferae |
| Cabbage root nematode | Heterodera cruciferae |
| Cactus cyst nematode | Cactodera cacti |
| Cajanus cyst nematode | Heterodera cajani |
| California dagger nematode | Xiphinema index |
| California meadow nematode | Pratylenchus neglectus |
| California root-lesion nematode | Pratylenchus neglectus |
| California sessile nematode | Cacopaurus epacris |
| Camel thorn cyst nematode | Heterodera oxiana |
| Camellia root-knot nematode | Meloidogyne camelliae |
| Canadian root-knot nematode | Meloidogyne microtyla |
| Carnation pin nematode | Paratylenchus curvitatus |
| Carnation pin nematode | Paratylenchus dianthus |
| Carolina spiral nematode | Scutellonema brachyurum |
| Carrot cyst nematode | Heterodera carotae |

TABLE 2-continued

| Common Name | Nematode Genus and species |
|---|---|
| Carrot root nematode | Heterodera carotae |
| Cereal cyst nematode | Heterodera avenae |
| Cereal cyst nematode | Heterodera latipons |
| Cereal root nematode | Heterodera avenae |
| Cereal root-knot nematode | Meloidogyne nassi |
| Cereals root eelworm | Heterodera major |
| Cereals root nematode | Heterodera avenae |
| Chamber's dagger nematode | Xiphinema chambersi |
| Christie's spiral nematode | Scutellonema christiei |
| Christie's stubby root nematode | Trichodorus christiei |
| Chrysanthemum foliar nematode | Aphelenchoides ritzemabosi |
| Chrysanthemum leaf nematode | Aphelenchoides ritzemabosi |
| Chrysanthemum nematode | Aphelenchoides ritzemabosi |
| Citrus nematode | Tylenchulus semipenetrans |
| Citrus ring nematode | Criconemoides citri |
| Citrus root nematode | Tylenchulus semipenetrans |
| Citrus root-knot nematode | Meloidogyne indica |
| Citrus spine nematode | Criconema civellae |
| Clover cyst nematode | Heterodera trifolii |
| Clover root nematode | Heterodera trifolii |
| Clover stem nematode | Ditylenchus dipsaci |
| Cobb's awl nematode | Dolichodorus heterocephalous |
| Cobb's lance nematode | Hoplolaimus galeatus |
| Cobb's meadow nematode | Pratylenchus penetrans |
| Cobb's ring nematode | Criconemoides simile |
| Cobb's root lesion nematode | Pratylenchus penetrans |
| Cobb's root-knot nematode | Nacobbus batatiformis |
| Cobb's spiral nematode | Helicotylenchus multicinctus |
| Cobb's stubby root nematode | Trichodorus primitivus |
| Coconut nematode | Rhadinaphelenchus cocophilus |
| Coconut palm nematode | Rhadinaphelenchus cocophilus |
| Cocopalm nematode | Rhadinaphelenchus cocophilus |
| Coffee meadow nematode | Pratylenchus coffeae |
| Coffee root-knot nematode | Meloidogyne exigua |
| Coffee root-lesion nematode | Pratylenchus coffeae |
| Columbia nematode | Hoplolaimus columbus |
| Columbia root-knot nematode | Meloidogyne chitwoodi |
| Corn cyst nematode | Heterodera zeae |
| Corn meadow nematode | Pratylenchus zeae |
| Corn root-lesion nematode | Pratylenchus zeae |
| Cotton root-knot nematode | Meloidogyne incognita acrita |
| Cowpea cyst nematode | Heterodera vigni |
| Crown-headed lance nematode | Hoplolaimus tylenchiformis |
| Currant nematode | Aphelenchoides ribes |
| Cyperus cyst nematode | Heterodera mothi |
| Cyst nematodes | Globodera spp. |
| Cyst nematodes | Heterodera spp. |
| Cyst-forming nematodes | Heterodera spp. |
| Cystoid body nematodes | Meloidoderita spp. |
| Cystoid nematodes | Meloidodera spp. |
| Dagger nematodes | Xiphinema spp. |
| De Man's meadow nematode | Pratylenchus pratensis |
| De Man's root-lesion nematode | Pratylenchus pratensis |
| Dock cyst nematode | Heterodera rosii |
| Douglas Fir nematode | Nacobbodera chitwoodi |
| Ear-cockle nematode | Anguina tritici |
| Estonian cyst nematode | Cactodera estonica |
| Eucalypt cystoid nematode | Cryphodera eucalypti |
| European dagger nematode | Xiphinema diversicaudatum |
| False root-knot nematode of sugar beets | Nacobbus batatiformis |
| False root-knot nematode | Nacobbus spp. |
| Fern nematode | Aphelenchoides fragariae |
| Fern nematode | Aphelenchoides olesistus |
| Fescue leaf gall nematode | Anguina graminis |
| Ficus cyst nematode | Heterodera fici |
| Fig cyst nematode | Heterodera fici |
| Fig pin nematode | Paratylenchus hamatus |
| Fig spine nematode | Criconema decalineatum |
| Foliar nematodes | Aphelenchoides spp. |
| Galeopsis cyst nematode | Heterodera galeopsidis |
| Galeopsis root nematode | Heterodera galeopsidis |
| Gall-forming nematodes | Meloidogyne spp. |
| Godfrey's meadow nematode | Pratylenchus brachyurus |
| Godfrey's root-lesion nematode | Pratylenchus brachyurus |
| Gold-plated nematode | Globodera rostochiensis |
| Golden nematode | Globodera rostochiensis |

TABLE 2-continued

| Common Name | Nematode Genus and species |
|---|---|
| Golden nematode of potato | Globodera rostochiensis |
| Grass cyst nematode | Punctodera punctata |
| Grass root-gall nematode | Subanguina radicicola |
| Grass sheath nematode | Hemicycliophora similis |
| Grass spiral nematode | Helicotylenchus erythrinae |
| Great root nematode | Heterodera avenae |
| Hairy-gall nematode | Nacobbus batatiformis |
| Heart-shaped cyst nematode | Heterodera cardiolata |
| Hop cyst nematode | Heterodera humuli |
| Hop nematode | Heterodera humuli |
| Hop root nematode | Heterodera humuli |
| Horsenettle cyst nematode | Globodera tabacum virginiae |
| Indian root-knot nematode | Meloidogyne brevicauda |
| Iris nematode | Ditylenchus destructor |
| Japanese cyst nematode | Heterodera elachista |
| Javanese root-knot nematode | Meloidogyne javanica |
| Kansas cyst nematode | Heterodera longicolla |
| Kidney-shaped nematode | Rotylenchulus reniformis |
| Kikuyu grass nematode | Meloidogyne kikuyuensis |
| Knapweed nematode | Mesoanguina picridis |
| Knawel cyst nematode | Heterodera scleranthii |
| Knotweed cyst nematode | Cactodera weissi |
| Kona coffee root-knot nematode | Meloidogyne konaensis |
| Lance nematodes | Hoplolaimus spp. |
| Lesion nematodes | Pratylenchus spp. |
| Lespedeza cyst nematode | Heterodera lespedezae |
| Lucerne cyst nematode | Heterodera medicaginis |
| Maple root-knot nematode | Meloidogyne ovalis |
| Meadow nematodes | Pratylenchus spp. |
| Mediterranean cereal cyst nematode | Heterodera latipons |
| Milfoil cyst nematode | Globodera millefolii |
| Motha cyst nematode | Heterodera mothi |
| Mushroom nematode | Aphelenchoides composticola |
| Mushroom spawn nematode | Ditylenchus myceliophagus |
| Needle nematodes | Longidorous spp. |
| Nettle cyst nematode | Heterodera urticae |
| Nigerian dagger nematode | Xiphinema nigeriense |
| Northern root-knot nematode | Meloidogyne hapla |
| Nutgrass cyst nematode | Heterodera cyperi |
| Oak root-knot nematode | Meloidogyne querciana |
| Oak sheathoid nematode | Hemicriconemoides biformis |
| Oat cyst nematode | Heterodera avenae |
| Oat cyst nematode | Heterodera major |
| Oat nematode | Heterodera avenae |
| Oat root nematode | Heterodera avenae |
| Onion stem nematode | Ditylenchus dipsaci |
| Osborne's cyst nematode | Globodera tabacum solanacearum |
| Pacific dagger nematode | Xiphinema radicicola |
| Pea cyst nematode | Heterodera goettingiana |
| Pea root eelworm | Heterodera goettingiana |
| Pea root nematode | Heterodera goettingiana |
| Peanut root-knot nematode | Meloidogyne arenaria |
| Persian sessile nematode | Cacopaurus pestis |
| Phlox stem nematode | Ditylenchus dipsaci |
| Pigeon pea cyst nematode | Heterodera cajani |
| Pin nematodes | Paratylenchus spp. |
| Pine cystoid nematode | Meloidodera floridensis |
| Pine sheathoid nematode | Hemicriconemoides floridensis |
| Pine sting nematode | Belonolaimus gracilis |
| Pine wood nematode | Bursaphelenchus xylophilus |
| Potato cyst eelworm | Globodera rostochiensis |
| Potato cyst nematode | Globodera pallida |
| Potato cyst nematode | Globodera rostochiensis |
| Potato nematode | Globodera rostochiensis |
| Potato root eelworm | Globodera rostochiensis |
| Potato root nematode | Globodera rostochiensis |
| Potato rot nematode | Ditylenchus destructor |
| Potato tuber eelworm | Ditylenchus destructor |
| Potato tuber nematode | Ditylenchus destructor |
| Pseudo root-knot nematode | Hypsoperine graminis |
| Ramie pin nematode | Paratylenchus elachistus |
| Red ring nematode | Rhadinaphelenchus cocophilus |
| Reniform nematode | Rotylenchulus reniformis |
| Reniform nematodes | Rotylenchulus spp. |
| Rice blind root nematodes | Hirschmanniella spp. |
| Rice cyst nematode | Heterodera oryzae |
| Rice nematode | Aphelenchoides oryzae |
| Rice root nematode | Hirschmanniella oryzae |
| Rice root-knot nematode | Meloidogyne graminicola |
| Rice stem nematode | Ditylenchus angustus |
| Rice stunt nematode | Tylenchorhynchus martini |
| Rice white-tip nematode | Aphelenchoides besseyi |
| Rice-root nematode | Radopholus oryzae |
| Ring nematodes | Criconema spp. |
| Ring nematodes | Criconemoides spp. |
| Root nematodes | Heterodera spp. |
| Root nematodes | Hirschmanniella spp. |
| Root-gall nematodes | Meloidogyne spp. |
| Root-knot nematodes | Meloidogyne spp. |
| Root-lesion nematodes | Pratylenchus spp. |
| Round cystoid nematode | Thecavermiculatus andinus |
| Rubber cyst nematode | Heterodera fici |
| Rumex cyst nemtode | Heterodera rumicis |
| Scribner's lesion nematode | Pratylenchus scribneri |
| Scribner's meadow nematode | Pratylenchus scribneri |
| Scribner's root-lesion nematode | Pratylenchus scribneri |
| Sedge cyst nematode | Heterodera cyperi |
| Seed gall nematode | Afrina wevelli |
| Seed gall nematodes | Anguina spp. |
| Seed-gall nematode | Anguina tritici |
| Seinhorst's stubby root nematode | Trichodorus pachydermis |
| Sessile nematodes | Cacopaurus spp. |
| Seville root-knot nematode | Meloidogyne hispanica |
| Sheath nematodes | Hemicycliophora spp. |
| Sheathoid nematodes | Hemicriconemoides spp. |
| Shoot gall nematodes | Anguina spp. |
| Smooth-headed lesion nematode | Pratylenchus brachyurus |
| Smooth-headed meadow nematode | Pratylenchus leiocephalus |
| Smooth-headed nematode | Pratylenchus brachyurus |
| Sorghum root-knot nematode | Meloidogyne acronea |
| Sour paste nematode | Panagrellus redivivus |
| South African pin nematode | Paratylenchus curvitatus |
| Southern root-knot nematode | Meloidogyne incognita |
| Sowthistle cyst nematode | Heterodera sonchophila |
| Soybean cyst nematode | Heterodera glycines |
| Spear nematodes | Dorylaimus spp. |
| Spine nematodes | Criconema spp. |
| Spiral nematodes | Helicotylenchus spp. |
| Spiral nematodes | Rotylenchus spp. |
| Spiral nematodes | Scutellonema spp. |
| Spring crimp nematode | Aphelenchoides fragariae |
| Spring dwarf nematode | Aphelenchoides besseyi |
| Steiner's spiral nematode | Helicotylenchus dihystera |
| Stem gall nematode | Pterotylenchus cecidogenus |
| Stem nematode | Ditylenchus dipsaci |
| Sting nematode | Belonolaimus gracilis |
| Sting nematode | Belonolaimus longicaudatus |
| Sting nematodes | Belonolaimus spp. |
| Strawberry bud nematode | Aphelenchoides besseyi |
| Strawberry bud nematode | Aphelenchoides fragariae |
| Strawberry foliar nematode | Aphelenchoides fragariae |
| Strawberry nematode | Aphelenchoides fragariae |
| Stubby root nematode | Trichodorus christiei |
| Stubby root nematode | Trichodorus kurumeensis |
| Stubby root nematodes | Paratrichodorus spp. |
| Stubby root nematodes | Trichodorus spp. |
| Stunt nematode | Tylenchorhynchus claytoni |
| Stunt nematodes | Tylenchorhynchus spp. |
| Stylet nematodes | Tylenchorhynchus spp. |
| Sugar beet cyst nematode | Heterodera schachtii |
| Sugar beet nematode | Heterodera schachtii |
| Sugar cane cyst nematode | Heterodera sacchari |
| Sugar cane cyst nematode | Heterodera schachtii |
| Sugar cane stylet nematode | Tylenchorhynchus martini |
| Summer dwarf nematode | Aphelenchoides fragariae |
| Sycamore root-knot nematode | Meloidogyne platani |
| Tadzhik cyst nematode | Heterodera tadshikistanica |
| Tadzhik cystoid nematode | Meloidodera tadshikistanica |
| Tadzhik root-knot nematode | Meloidogyne tadshikistanica |
| Tarjan's sheath nematode | Hemicycliophora parvana |
| Tea root-knot nematode | Meloidogyne brevicauda |
| Teasel nematode | Ditylenchus dipsaci |
| Tesselate stylet nematode | Tylenchorhynchus claytoni |
| Thames' root-knot nematode | Meloidogyne thamesi |

TABLE 2-continued

| Common Name | Nematode Genus and species |
| --- | --- |
| Thorne's cyst nematode | Cactodera thornei |
| Thorne's lance nematode | Rotylenchus uniformis |
| Thorne's meadow nematode | Pratylenchus thornei |
| Thorne's needle nematode | Longidorus sylphus |
| Thorne's root-lesion nematode | Pratylenchus thornei |
| Tobacco cyst nematode | Globodera tabacum |
| Tobacco stunt nematode | Tylenchorhynchus claytoni |
| Tulip root nematode | Ditylenchus dipsaci |
| Turf spiral nematode | Rotylenchus christiei |
| Turkmen cyst nematode | Heterodera turcomanica |
| Ustinov cyst nematode | Heterodera ustinovi |
| Valentine cyst nematode | Heterodera cardiolata |
| Vinegar eels | Turbatrix aceti |
| Vinegar nematode | Turbatrix aceti |
| Walnut meadow nematode | Pratylenchus vulnus |
| Walnut root-lesion nematode | Pratylenchus vulnus |
| Walnut sessile nematode | Cacopaurus pestis |
| Wesson's sheathoid nematode | Hemicriconemoides wessoni |
| West African spiral nematode | Scutellonema blaberum |
| Wheat cyst nematode | Heterodera latipons |
| Wheat gall nematode | Anguina tritici |
| White-tip nematode | Aphelenchoides besseyi |
| Willow cyst nematode | Heterodera salixophila |
| Yam nematode | Scutellonema bradys |
| Yarrow cyst nematode | Globodera achilleae |
| Zimmerman's spiral nematode | Helicotylenchus erythrinae |
| Zoysia spine nematode | Criconema spinalineatum |

24.0 Treating a Parasitic Nematode Infection

In certain embodiments of the present invention, a parasitic nematode infection is treated in an infected organism (including plants and animals). A preferred method of treating a parasitic nematode infection is to inhibit nematode fertility or reproduction in the infected animal. In general, this is done by administering a therapeutically effective amount of an anti-nematode agent as described herein which disrupts a biological activity of MSP related to female nematode sexual maturation. The anti-nematode agent can be identified as described in the present invention.

In certain embodiments, a method of inhibiting a reproduction of a nematode is provided, comprising inhibiting a signal transduction of a major sperm protein of the nematode, wherein the signal transduction stimulates a female sexual maturation.

In certain embodiments, MSP signal transduction is inhibited by a method comprising administering an MSP-specific antibody (Several MSP-specific antibodies have been described in the art. For example, see, Klass, M. R., and Hirsh, D. 1981. Sperm isolation and biochemical analysis of the major sperm protein from *Caenorhabditis elegans*. Dev. Biol. 84, 299–312, incorporated herein by reference). (In certain examples, the MSP-specific antibody can be administered by solublizing the antibody in the nematode's environment or by microinjection into the uterus of the nematode. Without being bound to mechanism or theory, these antibodies bind MSP in vivo and inhibit MSP-mediated signaling. Experiments are contemplated wherein hermaphrodite oocyte maturation and sheath cell contraction rates will be compared to hermaphrodites injected with an antibody which does not bind MSP (a suitable antibody for a negative control experiment).

In certain embodiments, MSP signal transduction is inhibited by administering a vaccine (especially in the case of treating an animal) wherein the vaccine is developed to an MSP protein or fragment thereof. Any variety of MSP protein, or fragment thereof, can be used in vaccine development. Many nematode types are described herein and the MSP or MSPs isolated therefrom may be used. Vaccine development protocols are well known.

In certain embodiments the identified anti-nematode agent is applied to crops including by spraying a field to distribute the agent. The agent may gain access directly to the nematode or exist in the soil, water, food or general environment of the nematode. The agent may also be transferred to the nematode from a plant or animal.

25.0 Pharmaceutical Formulations

In certain embodiments, the preferred method of administering a biologically active molecule (such as MSP or an anti-nematode agent) is in combination with an excipient (a pharmaceutically acceptable carrier). The combination of at least one pharmaceutically acceptable carrier and at least one biologically active molecule is referred to herein as a pharmaceutical formulation.

The particular excipient is not believed to be critical as long as it is compatible with the biological activity of the biologically active molecule and compatible with administration to the subject, especially plants, animals, human, and other mammals. The choice of excipient depends on the nature of the treatment being administered and the biologically active molecule. The pharmaceutical formulation can be applied to the surface of the organism being treated for a parasitic nematode infection or injected into the local tissue either in one application or multiple applications. The pharmaceutical formulation can be combined with additional inert or carrier ingredients and used as a topical salve. The pharmaceutical formulation may also be aerosolized an administered through the lungs.

In certain preferred embodiments, a pharmaceutical formulation is provided along with a method of applying a metered amount of the formulation. For example, if a syringe may include unit markings on the barrel of the syringe. Typically a syringe will also include a needle and a plunger to form a device effective for administration by injection. The particular choice of pharmaceutically acceptable carrier can be made by one with skill in the art, such as a treating physician, veterinarian, farmer, or extension service personnel.

As used herein, "pharmaceutically acceptable carrier" includes any and all solvents, dispersion media, coatings, antibacterial and antifungal agents, isotonic and absorption delaying agents and the like that are compatible with the biologically active molecule(s) and with administration to the organism being treated.

In certain embodiments, the pharmaceutical formulations of the present invention are advantageously administered either as liquid solutions or suspensions. Solid forms may be solubilized or suspended in liquid prior to application or injection. These preparations also may be emulsified. In certain embodiments, a typical composition comprises about 50 mg or up to about 100 mg of human serum albumin per milliliter of phosphate buffered saline. Other pharmaceutically acceptable carriers include aqueous solutions, salts, preservatives, buffers and the like. Examples of non-aqueous solvents are propylene glycol, polyethylene glycol, vegetable oil, and organic esters, such as theyloleate. Aqueous carriers include water, alcoholic/aqueous solutions, and saline solutions including sodium chloride, Ringer's dextrose, etc. Preservatives include antimicrobial agents, anti-oxidants, chelating agents and inert gases. The pH and exact concentration of the various components in the pharmaceutical formulation are adjusted according to well known parameters using well known buffering and dilution agents.

26.0 Production of Recombinant MSP Containing Vectors

Recombinant MSP bacterial strains were produced by cloning MSP-142 and MSP-38 into the pQe-30 6-His vector from Qiagen. Primers specific for MSP were made that contained a 5' BamHI site (5' primer) or a 5' HindIII (3' primer) followed by the respective MSP-coding sequences. MSP-38 and MSP-142 were amplified by PCR, cut with BamHI and HindIII, and ligated into the pQe-30 vector (FIGS. 6A and 6B) which was also cut with BamHI and HindIII. This strategy generated a vector containing an IPTG-inducible promoter followed by an initiator methionine, an N-terminal 6-His tag, and the respective MSP-38 or MSP-142 coding sequences. This construct was then transformed into M15(pREP4) bacterial cells and vector-containing colonies were selected with LB medium containing Ampicillin and Kanamycin. MSP-containing colonies were grown overnight and then MSP expression was induced for 4 hours with 1 mM IPTG. Induced bacteria were pelleted, lysed, and purified using a NiNTA agarose column, which binds the 6-His tag. 6-His purification is known in the art.

27.0 Biological Functional Equivalents of Polynucleotides and Polypeptides

As is known to one with skill in the art, the biological function or activity of a gene product may not correspond directly to an absolute polynucleotide or polypeptide sequence of the gene product. Therefore, the inventor specifically contemplates that alterations to sequences provided herein may be made or used wherein the altered sequences, or methods of use thereof, are equivalent to sequences, or methods of use thereof, and are within the spirit and scope of the present invention. These equivalent sequences are referred to as biologically functional equivalents, or simply as functional equivalents. Functional equivalents can include, but are not limited to: conservatively modified variants, degeneracy of the nucleic acid code, polymorphisms, certain insertions and deletions, and certain length variants. Methods for altering sequence residues and testing the altered sequences for function or activity are known in the art or described herein. These alterations may be natural or made by the "hand of man".

At the nucleotide level, different codons can encode the same amino acid. In other words, the genetic code is degenerate (Alberts et al., Molecular Biology of the Cell, (1989) 2nd Edition, Garland Publishing, Inc., and incorporated herein by reference). The terms "wobble" and "nucleic acid degeneracy" are used herein to refer to codons that encode the same amino acid, such as the six codons for arginine or serine. Preferred human codons are provided in materials appended to this application. Codon preferences for other organisms also are well known to those of skill in the art (Wada et al., 1990, supra). Thus, one with skill in the art knows that two different polynucleotides can encode identical polypeptide sequences due to codon wobble.

It is understood in the art that amino acid and nucleic acid sequences may include additional residues, such as additional N-terminal or C-terminal amino acids or 5' or 3' sequences, and yet still be essentially as set forth in one of the sequences disclosed herein; so long as the sequence meets the criteria set forth herein, including the maintenance of at least one biological protein activity where protein expression is concerned (MSP activity should include at least one type of stimulation of female nematode sexual maturation). The addition of terminal sequences particularly applies to nucleic acid sequences that may, for example, include various non-coding sequences flanking either of the 5' or 3' portions of the coding region or may include various internal sequences, i.e., introns, which are known to occur within genes between coding regions (Alberts et al., supra, incorporated herein by reference). Thus; about 1, 2, 3, 4, 5, 6, 7, or more than 7 amino acids could be added to a polypeptide and the polypeptide may still retain at least one biological activity. Or; about 1, 2, 3, 4, 5, 6, 7, or more than 7 nucleotides could be added to a polynucleotide and expression products of the polynucleotide may still retain at least one biological activity.

It also is understood in the art that amino acid and nucleic acid residues may be removed from the N-terminal or C-terminal ends of polypeptide or 5' or 3' ends of polynucleotide sequences, and yet still be essentially as set forth in one of the sequences disclosed herein; so long as the sequence meets the criteria set forth herein, including the maintenance of at least one biological protein activity of where protein expression is concerned (in particular stimulating a female nematode sexual maturation with regard to MSP). The removal of terminal sequences particularly applies to nucleic acid sequences that may, for example, include various non-coding sequences flanking either of the 5' or 3' portions of the coding region or may include various internal sequences, i.e., introns, which are known to occur within genes between coding regions (Alberts et al., supra, incorporated herein by reference). Thus; about 1, 2, 3, 4, 5, 6, 7, or more than 7 amino acids could be removed from a polypeptide and the polypeptide may still retain at least one biological activity. Or, about 1, 2, 3, 4, 5, 6, 7, or more than 7 nucleotides could be removed from a polynucleotide and expression products of the polynucleotide may still retain at least one biological activity.

If desired, it is possible using techniques known to one with skill in the art, to include an intron in a recombinant polynucleotide sequence. For example, a bovine growth hormone (bGH) intron including splice sites may be added. In certain instances, the addition of an intron to a recombinant polynucleotide has been observed to increase expression of the encoded expression product in eukaryotic cells. It is understood that the addition of an intron may create a functionally equivalent sequence.

It is further understood in the art that insertions and deletions may be made within the amino acid and nucleic acid sequence, and yet still be essentially as set forth in one of the sequences disclosed herein; so long as the sequence meets the criteria set forth herein, including the maintenance of biological protein activity where protein expression is concerned (for MSP this should be a stimulation of at least one female nematode sexual maturation). It is preferred that the reading frame of a polynucleotide sequence be maintained, as is known in the art (Alberts et al., supra, incorporated herein by reference).

Excepting intronic or flanking regions, and allowing for the degeneracy of the genetic code, sequences that have between about 70% and about 79%; or more preferably, between about 80% and about 89%; or more preferably, between about 90% and about 95% or more; or even more preferably, between about 96% and about 99%, or more of nucleotides being identical are homologous nucleic acids. Homologous sequences may be functionally defined as sequences that are capable of hybridizing to a nucleic acid segment under relatively stringent conditions. Suitable relatively stringent hybridization conditions are well known to those of skill in the art. In certain embodiments, relatively stringent hybridization conditions allow hybridization between sequences with about 70% homology or more, but disrupt binding between sequences with less than 70% homology. In certain embodiments, sequences that are considered "essentially as set forth" in a sequence listed herein are also biologically functional equivalents to the listed sequence if at least one biological activity is found in common.

At the protein level, peptide sequences that are essentially the same, in general, are capable of cross-reacting with antibody raised against the respective peptide factor. Methods for isolating, resolving, and analyzing protein/antibody interactions are well known in the art including techniques such as SDS-PAGE and Western analysis.

The nucleic acid segments of the present invention, regardless of the length of the coding sequence itself, may be combined with other DNA sequences (one or more of each), such as promoters, polyadenylation signals, additional restriction enzyme sites, multiple cloning sites, internal ribosome entry sites, introns, other coding segments, membrane transport sequences, and the like, such that their overall length may vary considerably. It is therefore contemplated that a nucleic acid fragment of almost any length may be employed, with the total length preferably being limited by the ease of preparation and use in the intended recombinant DNA protocol. Therefore, the terms "MSP gene" may also comprise any combination of associated control sequences. Furthermore, those skilled in the art of mutagenesis will appreciate that other analogs, as yet undisclosed or undiscovered, may be used to construct MSP analogs (mutants, variants, etc). Additional meaning of biological functional equivalents, similarity, percent similarity, equivalents, substantially identical sequences, essentially the same, and essentially similar sequences and activities are described in U.S. Pat. No. 5,922,688 to Hung et al., incorporated herein by reference.

Naturally, the present invention also encompasses peptides and polypeptides (or the nucleic acid sequences that encode such peptides and polypeptides) that contain conservatively modified variants of sequences of interest, for example, a MSP sequence. One with skill in the art is able to determine conservative sequence modifications. In the case of a polypeptide, amino acid substitutions, such as those which might be employed in modifying a peptide, such as MSP, are generally based on the relative similarity of the amino acid side-chain substituents, for example, their hydrophobicity, hydrophilicity, charge, size, and the like.

An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as conservative amino acid changes or substitutions. In general, conservatively modified variants of a sequence may include one or more conservative amino acid change or substitution.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., J. Mol. Biol. (1982) 157(1):105–32, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101 to Hopp, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, supra, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on conservatively modified variant polypeptides and functionally equivalent polypeptides arising from amino acid changes, it will be appreciated that these changes may be effected by alteration of the encoding polynucleotide; taking into consideration also that the genetic code is degenerate and that two or more codons may code for the same amino acid.

28.0 Sequence Modification Techniques

Modifications to sequences, such as MSP sequences, may be made during chemical synthesis of the polymers (either nucleotide or peptide synthesis). It is believed, however, that site-directed mutagenesis of an encoding nucleic acid, creating a suitably altered polynucleotide sequence is the most cost effective method of generating an altered polynucleotide sequence. Where the MSP protein is desired, then the mutated sequence may be expressed including in culture (in vitro or ex vivo) or in vivo.

Site-directed mutagenesis is a technique useful in the preparation of individual peptides, or biologically functional equivalent proteins or peptides, through specific mutagenesis of the underlying DNA. Several methods for site directed mutagenesis are described in U.S. Pat. No. 4,873,192 to Kunkel, incorporated herein by reference and in U.S. Pat. No. 4,351,901 to Ball, incorporated herein by reference. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to 10 residues on both sides of the junction of the sequence being altered.

The primers can be selected by one with ordinary skill in the art based upon information provided herein, including the Sequence Listings and Figures.

The technique of site-specific mutagenesis is well known in the art as exemplified by publications (Adelman et al., (1983) DNA 2(3)183–193, incorporated herein by reference). As will be appreciated, the technique typically employs a phage vector which exists in both a single stranded and double stranded form. Typical vectors useful in site-directed mutagenesis include vectors such as the M13 phage. These phage are readily commercially available and their use is well known to those skilled in the art. Double stranded plasmids are also routinely employed in site directed mutagenesis which eliminates the step of transferring the gene of interest from a plasmid to a phage. Kits for phage based site directed mutagenesis are commercially available. In addition PCR based methods which may, or may not, involve phage are known in the art and kits for such purposes are commercially available.

In certain known techniques, site-directed mutagenesis is performed by first obtaining a single-stranded vector or melting apart the two strands of a double stranded vector which includes within its sequence a DNA sequence which encodes the desired nucleotide, such as MSP. An oligonucleotide primer bearing the desired mutated sequence is prepared, generally synthetically as is known to one of ordinary skill in the art. This primer is then annealed with the single-stranded vector, and subjected to DNA polymerizing enzymes such as *Escherichia coli* (*E. coli*) polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement. Various selection methods that increase the percentage of specifically modified clones over wild-type are known and available commercially.

Kalderon et al. (1984) report several mutagenic methods which have proved useful in mutating the native LT gene. Specifically, Kalderon et al. teach deletion mutations by displacement-loop mutagenesis and by the random insertion of Eco RI linkers into the LT gene. Further, point mutation by deletion-loop mutagenesis is taught. The reference also teaches screening procedures for determining the success of such mutations. The teachings of Kalderon et al. (1984) Virology 139(1)109–137 are incorporated herein by reference.

The preparation of sequence variants of the selected gene using site-directed mutagenesis is provided as a method of producing potentially useful nucleic acids and peptides (such as MSP and MSP variants) and is not meant to be limiting as there are other ways in which sequence variants of these nucleotide and peptides may be obtained. For example, recombinant vectors encoding the desired genes may be treated with mutagenic agents to obtain sequence variants for the mutagenesis of plasmid DNA using hydroxylamine or random mutagenesis may be performed using the PCR technique.

Sequence analysis of a potentially mutant nucleic acid sequence is carried out by methods known in the art, typically by either Sanger dideoxy sequencing (Sanger et al., PNAS (1977) 74:5363–5467, incorporated herein by reference; U.S. Pat. No. 4,871,929 to Barnes; and U.S. Pat. No. 4,962,020 to Tabor et al., each patent incorporated herein by reference) or automated sequencing (U.S. Pat. No. 5,365,455 to Tibbetts et al., incorporated herein by reference).

In addition to the MSP peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Livestock include, but are not limited to: horses, work horses, show horses, cattle, sheep, goats, and the like. Pets include, but are not limited to: dogs, cats, horses, birds, and the like.

EXAMPLES

Example 1

Large quantities of sperm (generally >108) are purified using a modification of methods developed by Klass and Hirsh (1981). Adult males are identified using synchronized cultures (Lewis and Flemming, 1995) of fog-2(q71), which are 50% male and 50% female. Mutations in the fog-2 gene block spermatogenesis in XX animals, transforming them into females, but have no effect on X0 animals, which are fertile males (Schedl and Kimble, 1988). Males are separated from females, larvae, and embryos based on size by sieving through NITEX screens of various pore sizes. The populations of males isolated in this way are generally >99% pure. To isolate sperm, males are placed between two PLEXIGLASS plates and smashed in a vice grip (The Home Depot, Inc.). Intact sperm are then purified from the carcasses by filtration through NITEX filters (20 micron pore size) and washed in M9 phosphate buffer (Sulston and Hodgkin, 1988) using several rounds of low speed centrifugation (e.g., 10,000×g) and resuspension. Sperm-conditioned medium (SCM) is prepared by incubating purified sperm in M9 for different periods of time (1–12 h) and subsequently removing the sperm by centrifugation and filtration through a 0.2 micron filter. Microscopic analysis suggests that the sperm are not lysing during the incubation. Polyacrylamide gel electrophoresis (PAGE) further indicaets that the sperm are not lysing during the incubation, but that a 14 kDa protein is enriched in SCM (FIG. 2).

REFERENCES

All references, articles, U.S. Patents, Non-U.S. Patents, exhibits and the like referred to herein, including those listed below or attached, are hereby incorporated herein by reference in their entirety.

Achanzar, W. E., and Ward, S. (1997). A nematode gene required for sperm vesicle fusion. Journal of Cell Science 110: 1073–1081.

Albertson, D. G. (1984). Formation of the first cleavage spindle in nematode embryos. Developmental Biology 101: 61–72.

Albertson, D. G., and Thomson, J. N. (1993). Segregation of holocentric chromosomes at meiosis in the nematode, *Caenorhabditis elegans*. Chromosome Research 1: 15–26.

Anderson, E., and Albertini, D. F. (1976). Gap junctions between the oocyte and companion follicle cells in the mammalian ovary. Journal of Cell Biology 71: 680–686.

Argon, Y., and Ward, S. (1980). *C. elegans* fertilization-defective mutants with abnormal sperm. Genetics 96: 413–433.

Aroian, R. V., Field, C., Pruliere, G., Kenyon, C., and Alberts, B. M. (1997). Isolation of actin-associated proteins from *Caenorhabditis elegans* oocytes and their localization in the early embryo. EMBO Journal 16: 1541–1549.

Aruffo, A., and Seed, B. (1987). Molecular cloning of a CD28 cDNA by a high-efficiency COS cell expression system. Proceedings of the National Academy of Sciences USA 84: 8573–8577.

Austin, J., and Kimble, J. (1987). glp-1 is required in the germ line for regulation of the decision between mitosis and meiosis in *C. elegans*. Cell 51: 589–599.

Barton, M. K., and Kimble, J. (1990). fog-1, a regulatory gene required for specification of spermatogenesis in the germ line of *Caenorhabditis elegans*. Genetics 125: 29–39.

Bashir, R., Britton, S., Strachan, T., Keers, S., Vafiadaki, E., Lako, M., Richard, I., Marchand, S,. Bourg, N., Argov, Z., Sadeh, M., Mahjneh, I., Marconi, G., Passos-Bueno, M. R., Moreira, E. de S., Zatz, M., Beckmann, J. S., and Bushby, K. (1998). A gene related to *Caenorhabditis elegans* spermatogenesis factor fer-1 is mutated in limb-girdle muscular dystrophy type 2B. Nature Genetics 20: 37–42.

Blaxter, M. (1998). *Caenorhabditis elegans* is a nematode. Science 282: 2041–2046.

Boxem, M., Srinivasan, D. G., and van den Heuvel, S. (1999). The *Caenorhabditis elegans* gene ncc-1 encodes a cdc2-related kinase required for M phase in meiotic and mitotic cell divisions, but not for S phase. Development 126: 2227–2239.

Brenner, S. (1974). The genetics of *Caenorhabditis elegans*. Genetics 77: 71–94.

Browning, H., and Strome, S. (1996). A sperm-supplied factor required for embryogenesis in *C. elegans*. Development 122: 391–404.

Bullock, T. L., Roberts, T. M., and Stewart, M. (1996). 2.5 A resolution crystal structure of the motile major sperm protein (MSP) of *Ascaris suum*. Journal of Molecular Biology 263: 284–296.

*C. elegans* Sequencing Consortium. (1998). Genome sequence of the nematode *Caenorhabditis elegans*: A platform for investigating biology. Science 282: 2012–2018.

Cadigan, K. M., and Nusse, R. (1997). Wnt signaling: a common theme in animal development. Genes and Development 11: 3286–3305.

Chase, D., Serafinas, C., Ashcroft, N., Kosinski, M., Longo, D., Ferris, D. K., and Golden, A. (2000). The polo-like kinase PLK-1 is required for nuclear envelope breakdown and the completion of meiosis in *Caenorhabditis elegans*. Genesis: The Journal of Genetics and Development 26: 26–41.

Chen, P. J., Singal, A., Kimble, J., and Ellis, R. E. (2000). A novel member of the Tob family of proteins controls sexual fate in *Caenorhabditis elegans* germ cells. Developmental Biology 217: 77–90.

Church, D. L., Guan, K.-L., and Lambie, E. J. (1995). Three genes of the MAP kinase cascade, mek-2, mpk-1/sur-1 and let-60 ras, are required for meiotic cell cycle progression in *Caenorhabditis elegans*. Development 121: 2525–2535.

Clandinin, T. R., DeModena, J. A., and Sternberg, P. W. (1998). Inositol triphosphate mediates a RAS-independent response to LET-23 receptor tyrosine kinase activation in *C. elegans*. Cell 92: 523–533.

Colledge, W. H., Carlton, M. B. L., Udy, G. B., and Evans, M. J. (1994). Disruption of c-mos causes parthenogenetic development of unfertilized mouse eggs. Nature 370: 65–68.

Cordero, M. M., Cornish, T. J., Cotter, R. J., and Lys, I. A. (1995). Sequencing peptides without scanning the reflectron: post-source decay with a curved-field reflectron time-of-flight mass spectrometer. Rapid Communications in Mass Spectrometry 9: 1356–1361.

Coulson, A., Huynh, C., Kozono, Y., and Shownkeen, R. (1995). The physical map of the *Caenorhabditis elegans* genome. In: Epstein, H. F., and Shakes, D. C., editors. Methods in Cell Biology. *Caenorhabditis elegans:* Modern Biological Analysis of an Organism. San Diego: Academic Press. p. 533–550.

Cross, D. A., and Smythe, C. (1998). PD98059 prevents establishment of the spindle assembly checkpoint and inhibits the G2-M transition in meiotic but not mitotic cell cycles in *Xenopus*. Experimental Cell Research 241: 12–22.

Davis, S., Aldrich, T. H., Valenzuela, D. M., Wong, V. V., Furth, M. E., Squinto, S. P., and Yancopoulos, G. D. (1991). The receptor for ciliary neurotrophic factor. Science 253: 59–63.

Dernburg, A. F., McDonald, K., Moulder, G., Barstead, R., Dresser, M., and Villeneuve, A. M. (1998). Meiotic recombination in *C. elegans* initiates by a conserved mechanism and is dispensable for homologous chromosome synapsis. Cell 94: 387–398.

Ellis, R. E., and Kimble, J. (1995). The fog-3 gene and regulation of cell fate in the germ line of *Caenorhabditis elegans*. Genetics 139: 561–577.

Ferby, I., Blazquez, M., Palmer, A., Eritja, R., and Nebreda, A. R. (1999). A novel p34(cdc2)-binding and activating protein that is necessary and sufficient to trigger G(2)/M progression in *Xenopus* oocytes. Genes and Development 13: 2177–2189.

Ferrell, J. E., Jr. (1999). *Xenopus* oocyte maturation: new lessons from a good egg. BioEssays 21: 833–842.

Ferrell, J. E., Jr., Wu, M., Gerhart, J. C., and Martin, G. S. (1991). Cell cycle tyrosine phosphorylation of p34cdc2 and a microtubule-associated protein kinase homolog in *Xenopus* oocytes and eggs. Molecular and Cellular Biology 11: 1965–1971.

Fire, A., Xu, S., Montgomery, M. K., Kostas, S. A., Driver, S. E, and Mello, C. C. (1998). Potent and specific genetic interference by double-stranded RNA in *Caenorhabditis elegans*. Nature 391: 806–811.

Fisher, D. L., Brassac, T., Galas, S., and Doree, M. (1999). Dissociation of MAP kinase activation and MPF activation in hormone-stimulated maturation of *Xenopus* oocytes. Development 126: 4537–4546.

Francis, R., Barton, M. K., Kimble, J., and Schedl, T. (1995). gld-1, a tumor suppressor gene required for oocyte development in *Caenorhabditis elegans*. Genetics 139: 579–606.

Gavrilets, G., *Nature* 403, 886 (2000).

Godeau, J. F., Schorderet-Slatkine, S., Hubert, P., and Baulieu, E. E. (1978). Induction of maturation in *Xenopus laevis* oocytes by a steroid linked to a polymer. Proceedings of the National Academy of Sciences USA 75: 2353–2357.

Gotoh, Y., Masuyama, N., Dell, K., Shirakabe, K., and Nishida, E. (1995). Initiation of *Xenopus* oocyte maturation by activation of the mitogen-activated protein kinase cascade. Journal of Biological Chemistry 270: 25898–25904.

Gotoh, Y., Moriyama, K., Matsuda, S., Okumura, E., Kishimoto, T., Kawasaki, H., Suzuki, K., Yahara, I., Sakai, H., and Nishida, E. (1991). *Xenopus* M phase MAP kinase: isolation of its cDNA and activation by MPF. EMBO Journal 10:2661–2668.

Grant, B., and Hirsh, D. (1999). Receptor-mediated endocytosis in the *Caenorhabditis elegans* oocyte. Molecular Biology of the Cell 10: 4311–4326.

Greenstein, D., Hird, S., Plasterk, R. H. A., Andachi, Y., Kohara, Y., Wang, B., Finney, M., and Ruvkun, G. (1994). Targeted mutations in the *Caenorhabditis elegans* POU homeo box gene ceh-18 cause defects in oocyte cell cycle arrest, gonad migration, and epidermal differentiation. Genes and Development 8: 1935–1948.

Greenstein, D., unpublished results.

Gross, S. D., Schwab, M. S., Taieb, F. E., Lewellyn, A. L., Qian, Y. W., and Maller, J. L. (2000). The critical role of the MAP kinase pathway in meiosis II in *Xenopus* oocytes is mediated by p90(Rsk). Current Biology 10: 430–438.

Haaf, A., Butler, P. J., Kent, H. M., Fearnley, I. M., Roberts, T. M., Neuhaus, D., and Stewart, M. (1996). The motile major sperm protein (MSP) from *Ascaris suum* is a symmetric dimer in solution. Journal of Molecular Biology 260: 251–260.

Haccard, O., Lewellyn, A., Hartley, R. S., Erikson, E., and Maller, J. L. (1995). Induction of *Xenopus* oocyte meiotic maturation by MAP kinase. Developmental Biology 168: 677–682.

Hall, D. H., Winfrey, V. P., Blaeuer, G., Hoffman, L. H., Furuta, T., Rose, K. L., Hobert, O., and Greenstein, D. (1999). Ultrastructural features of the adult hermaphrodite gonad of *Caenorhabditis elegans*: relations between the germ line and soma. Developmental Biology 212: 101–123.

Hashimoto, N., Watanabe, N., Furuta, Y., Tamemoto, H., Sagata, N., Yokoyama, M., Okazaki, K., Nagayoshi, M., Takeda, N., Ikawa, Y., and Aizawa, S. (1994). Parthenogenetic activation of oocytes in c-mos deficient mice. Nature 370: 68–71.

Hill, D. P., Shakes, D. C., Ward, S., and Strome, S. (1989). A sperm-supplied product essential for initiation of normal embryogenesis in *Caenorhabditis elegans* is encoded by the paternal-effect embryonic-lethal gene, spe-11. Developmental Biology 136: 154–166.

Hill, K. L. and L'Hernault, S. W., submitted.

Hirsh, D., Oppenheim, D., and Klass, M. (1976). Development of the reproductive system of *Caenorhabditis elegans*. Developmental Biology 49: 200–219.

Holst, P. A., and Phemister, R. D. (1971). The prenatal development of the dog: Preimplantation events. Biology of Reproduction 5: 194–206.

Hooper, N. M., and Bashir, A. (1991). Glycosyl-phosphatidylinositol-anchored membrane proteins can be distinguished from transmembrane polypeptide-anchored proteins by differential solubilization and temperature-induced phase separation in Triton X-114. Biochemical Journal 280: 745–751.

Huang, W., Kessler, D. S., and Erikson, R. L. (1995). Biochemical and biological analysis of Mek1 phosphorylation site mutants. Molecular Biology of the Cell 6: 237–245.

Hubbard, E. J. A., and Greenstein, D. (2000). The *C. elegans* gonad: a test tube for cell and developmental biology. Developmental Dynamics 218: 2–22.

Hyttel, P., Farstad, W., Mondain-Monval, M., Bakke Lajord, K., and Smith, A. J. (1990). Structural aspects of oocyte maturation in the blue fox (*Alopex lagopus*). Anatomy and Embryology 181, 325–331.

Ishikawa, K., Hanaoka, Y., Kondo, Y., and Imai, K. (1977). Primary action of steroid hormone at the surface of amphibian oocyte in the induction of germinal vesicle breakdown. Molecular and Cellular Endocrinology 9: 91–100.

Italiano, J. E., Jr., Roberts, T. M., Stewart, M., and Fontana, C. A. (1982). Reconstitution in vitro of the motile apparatus from the amoeboid sperm of *Ascaris* shows that filament assembly and bundling move membranes. Cell 84: 105–114.

Jansen, G., Hazendonk, E., Thijssen, K. L., and Plasterk, R. H. (1997). Reverse genetics by chemical mutagenesis in *Caenorhabditis elegans*. Nature Genetics 17: 119–121.

Kagiwada, S., Hosaka, K., Murata, M., Nikawa, J., and Takatsuki, A. (1998). The *Saccharomyces cerevisiae* SCS2 gene product, a homolog of a synaptobrevin-associated protein, is an integral membrane protein of the endoplasmic reticulum and is required for inositol metabolism. Journal of Bacteriology 180: 1700–1708.

Kanatani, H., Shirai, H., Nakanishi, K., and Kurokawa, T. (1969). Isolation and identification on meiosis inducing substance in starfish *Asterias amurensis*. Nature 221: 273–274.

Kaufmann, R., Spengler, B., and Lutzenkirchen, F. (1993). Mass spectrometric sequencing of linear peptides by product-ion analysis in a reflectron time-of-flight mass spectrometer using matrix-assisted laser desorption ionization. Rapid Communications in Mass Spectrometry 7: 902–910.

Kimble, J., and Hirsh, D. (1979). The postembryonic cell lineages of the hermaphrodite and male gonads in *Caenorhabditis elegans*. Developmental Biology 70: 396–417.

Kirby, C., Kusch, M., and Kemphues, K. (1990). Mutations in the par genes of *Caenorhabditis elegans* affect cytoplasmic reorganization during the first cell cycle. Developmental Biology 142: 203–215.

Klass, M. R., and Hirsh, D. (1981). Sperm isolation and biochemical analysis of the major sperm protein from *C. elegans*. Developmental Biology 84: 299–312.

Kosako, H., Gotoh, Y., and Nishida, E. (1994). Requirement for the MAP kinase kinase/MAP kinase cascade in *Xenopus* oocyte maturation. EMBO Journal 3:2131–2138.

LaMunyon, C. W., and Ward, S. (1994). Assessing the viability of mutant and manipulated sperm by artificial insemination of *Caenorhabditis elegans*. Genetics 138: 689–692.

Laurent, F., Labesse, G., and de Wit, P. (2000). Molecular cloning and partial characterization of a plant VAP33 homologue with a major sperm protein domain. Biochemical and Biophysical Research Communications 270: 286–292.

Lee, M.-H. and Schedl, T., unpublished results.

Lewis, J. A., and Flemming, J. T. (1995). Basic culture methods. In: Epstein, H. F., and Shakes, D. C., editors. Methods in Cell Biology. *Caenorhabditis elegans*: Modern Biological Analysis of an Organism. San Diego: Academic Press. p. 3–29.

L'Hernault, S. W. (1997). Spermatogenesis. In: Riddle, D. L., Blumenthal, T., Meyer, B. J., and Priess, J. R., editors. *C. elegans* II. Cold Spring Harbor, New York: Cold Spring Harbor Laboratory Press. p. 271–294.

L'Hernault, S. W., and Roberts, T. M. (1995). Cell biology of nematode sperm. In: Epstein, H. F., and Shakes, D. C., editors. Methods in Cell Biology. *Caenorhabditis elegans:* Modern Biological Analysis of an Organism. San Diego: Academic Press. p. 273–301.

L'Hernault, S. W., Arduengo, P. M., *J. Cell Biol.* 119, 55 (1992).

Lin, R. J., Kao, H. Y., Ordentlich, P., and Evans, R. M. (1998). The transcriptional basis of steroid physiology. Cold Spring Harbor Symposium on Quantitative Biology 63: 577–585.

Liu, X., Kim, C. N., Yang, J., Ronald Jemmerson, R., and Wang, X. (1996). Induction of apoptotic program in cell-free extracts: requirement for dATP and cytochrome c. Cell 86: 147–157.

MacMorris, M., Spieth, J., Madej, C., Lea, K., and Blumenthal, T. (1994). Analysis of the VPE sequences in the *Caenorhabditis elegans* vit-2 promoter with extrachromosomal tandem array-containing transgenic strains. Molecular and Cellular Biology 14: 484–491.

Masui, Y., and Clarke, H. J. (1979). Oocyte maturation. International Review of Cytology 57: 185–282.

Masui, Y., and Markert, C. L. (1971). Cytoplasmic control of nuclear behavior during meiotic maturation of frog oocytes. Journal of Experimental Zoology 177: 129–145.

McCarter, J., Bartlett, B., Dang, T., and Schedl, T. (1997). Soma-germ cell interactions in *Caenorhabditis elegans*: Multiple events in germline development require the somatic sheath and spermathecal lineages. Developmental Biology 181: 121–143.

McCarter, J., Bartlett, B., Dang, T., and Schedl, T. (1999). On the control of oocyte meiotic maturation and ovulation in *C. elegans*. *Developmental Biology* 205: 111–128.

Mendez, R., Hake, L. E., Andresson, T., Littlepage, L. E., Ruderman, J. V., and Richter, J. D. (2000). Phosphorylation of CPE binding factor by Eg2 regulates translation of c-mos mRNA. Nature 404: 302–307.

Miller, M. A., Nguyen V. Q., Lee, M., Kosinski, M., Schedl, M., Caprioli, R. M., and Greenstein D. (2001) A Sperm Cytoskeletal Protein That Signals Oocyte Meiotic Maturation and Ovulation. *Science* 2001 291: 2144–2147.

Morgan, D. O. (1997). Cyclin-dependent kinases: engines, clocks, and microprocessors. Annual Review of Cell and Developmental Biology 13: 261–291.

Muhlrad, D., Hunter, R., and Parker, R. (1992). A rapid method for localized mutagenesis of yeast genes. Yeast 8: 79–82.

Mukherjee, S., Ghosh, R. N., and Maxfield, F. R. (1997). Endocytosis. Physiology Reviews 77: 759–803.

Munson, P. J., and Rodbard, D. (1980). Ligand: a versatile computerized approach for characterization of ligand-binding systems. Analytical Biochemistry 107: 220–239.

Myers, C. D., Goh, P.-Y., Allen, T. St. C., Bucher, E. A., and Bogaert, T. (1996). Developmental genetic analysis of Troponin T mutations in striated and nonstriated muscle cells of *Caenorhabditis elegans*. Journal of Cell Biology 132: 1061–1077.

Nance, J., Minniti, A. N., Sadler, C., and Ward, S. (1999). spe-12 encodes a sperm cell surface protein that promotes spermiogenesis in *Caenorhabditis elegans*. Genetics 152: 209–220.

Nelson, G. A., Roberts, T. M., and Ward, S. (1982). *C. elegans* spermatozoan locomotion: Amoeboid movement with almost no actin. Journal of Cell Biology 92: 121–131.

Nelson, G. A., and Ward, S. (1980). Vesicle fusion, pseudopod extension and amoeboid motility are induced in nematode spermatids by the ionophore monensin. Cell 19: 457–464.

Palmer, A. and Nebreda, A. R., *Prog. Cell Cycle Res.*4, 131 (2000).

Pandey, A., and Mann, M. (2000). Proteomics to study genes and genomes. Nature 405: 837–846.

Pavalko, F. M., and Roberts, T. M. (1989). Posttranslational insertion of a membrane protein on *Caenorhabditis elegans* sperm occurs without de novo protein synthesis. Journal of Cellular Biochemistry 41: 57–70.

Podbilewicz, B. (1996). ADM-1, a protein with metalloprotease- and disintegrin-like domains, is expressed in syncytial organs, sperm, and sheath cells of sensory organs in *Caenorhabditis elegans*. Molecular Biology of the Cell 7: 1877–1893.

Posada, J., and Cooper, J. A. (1992). Requirements for phosphorylation of MAP kinase during meiosis in *Xenopus* oocytes. Science 255: 212–215.

Qian, Y. W., Erikson, E., and Maller, J. L. (1999). Mitotic effects of a constitutively active mutant of the *Xenopus* polo-like kinase Plx1. Molecular and Cellular Biology 19: 8625–8632.

Ramalho-Santos, J., et al., *Dev. Biol.* 223, 54 (2000).

Resing, K. A., Mansour, S. J., Hermann, A. S., Johnson, R. S., Candia, J. M., Fukasawa, K., Vande Woude, G. F., and Ahn, N. G. (1995). Determination of v-Mos-catalyzed phosphorylation sites and autophosphorylation sites on MAP kinase by ESI/MS. Biochemistry 34: 2610–2620.

Roberts, T. M. (1983). Crawling *C. elegans* spermatozoa contact the substrate only by their pseudopods and contain 2-nm filaments. Cell Motility 3: 333–347.

Roberts, T. M., Pavalko, F. M., and Ward, S. (1986). Membrane and cytoplasmic proteins are transported in the same organelle complex during nematode spermatogenesis. Journal of Cell Biology 102: 1787–1796.

Roberts, T. M., and Stewart, M. (1995). Nematode sperm locomotion. Current Opinion in Cell Biology 7: 13–17.

Roberts, T. M., and Stewart, M. (2000). Acting like actin. The dynamics of the nematode major sperm protein (msp) cytoskeleton indicate a push-pull mechanism for amoeboid cell motility. Journal of Cell Biology 149: 7–12.

Roberts, T. M., and Ward, S. (1982a). Membrane flow during nematode spermiogenesis. Journal of Cell Biology 92: 113–120.

Roberts, T. M., and Ward, S. (1982b). Centripetal flow of pseudopodial surface components could propel the amoeboid movement of *C. elegans* spermatozoa. Journal of Cell Biology 92: 132–138.

Rose, K. L., Winfrey, V. P., Hoffman, L. H., Hall, D. H., Furuta, T., and Greenstein D. (1997). The POU gene ceh-18 promotes gonadal sheath cell differentiation and function required for meiotic maturation and ovulation in *Caenorhabditis elegans*. Developmental Biology 192: 59–77.

Rutledge, E., Bianchi, L., Christensen, M., Morrison, R., Broslat, A., Beld, A., George Jr., A. L., Greenstein, D., and Strange, K. (2000). CLH-3: a *C. elegans* ClC-2 chloride channel orthologue regulated by cell cycle events and involved in soma-germline intercellular signaling. Submitted.

Sagata, N. (1997). What does Mos do in oocytes and somatic cells? BioEssays19: 13–21.

Sagata, N., Oskarsson, M., Copeland, T., Brumbaugh, J., and Vande Woude, G. F. (1988). Function of c-mos proto-oncogene product in meiotic maturation in *Xenopus* oocytes. Nature 335:519–525.

Sagata, N., Watanabe, N., Vande Woude, G. F., and Ikawa, Y. (1989). The c-mos proto-oncogene product is a cytostatic factor responsible for meiotic arrest in vertebrate eggs. Nature 342: 512–518.

Schagger, H., and von Jagow, G. (1987). Tricine-sodium dodecyl sulfate-polyacrylamide gel electrophoresis for the separation of proteins in the range from 1 to 100 kDa. Analytical Biochemistry 166: 368–379.

Schedl, T., and Kimble, J. (1988). fog-2, a germ-line-specific sex determination gene required for hermaphrodite spermatogenesis in *C. elegans*. Genetics 119: 43–61.

Schulz, J. R., et al., *J. Biol. Chem.* 273, 24355 (1998).

Seed, B., and Aruffo, A. (1987). Molecular cloning of the CD2 antigen, the T-cell erythrocyte receptor, by a rapid immunoselection procedure. Proceedings of the National Academy of Sciences USA 84: 3365–3369.

Shakes, D. C., and Ward, S. (1989). Initiation of spermiogenesis in *C. elegans*: A pharmacological and genetic analysis. Developmental Biology 134: 189–200.

Sheets, M. D., Wu, M., and Wickens, M. (1995). Polyadenylation of c-mos mRNA as a control point in *Xenopus* meiotic maturation. Nature 374: 511–516.

Skehel, P. A., Armitage, B. A., Bartsch, D., Hu, Y., Kaang, B. K., Siegelbaum, S. A., Kandel, E. R., and Martin, K. C. (1995). Proteins functioning in synaptic transmission at the sensory to motor synapse of *Aplysia*. Neuropharmacology 34: 1379–1385.

Skehel, P. A. et al., *Science* 269, 1580 (1995).

Smith, H. E., and Ward, S. (1998). Identification of protein-protein interactions of the major sperm protein (MSP) of *Caenorhabditis elegans*. Journal of Molecular Biology 279: 605–619.

Smith, L. D., and Ecker, R. E. (1969). Role of the oocyte nucleus in physiological maturation in *Rana pipiens*. Developmental Biology 19: 281–309.

Smith, L. D., and Ecker, R. E. (1971). The interaction of steroids with *Rana pipiens* oocytes in the induction of maturation. Developmental Biology 25: 232–247.

Soussan, L. et al., *J. Cell Biol.* 146, 301 (1999).

Spector, D. L., Goldman, R. D., and Leinwand, L. A. (1998). Plasma membrane isolation using the cationic colloidal silica isolation technique. In Culture and Biochemical Analysis of Cells. K. Janssen, editor. p. 35.1–35.14. Cold Spring Harbor Laboratory Press: Plainview, N.Y.

Starck, J., Gibert, M.-A., Brun, J., and Bosch C. (1983), Ribosomal RNA synthesis and processing during oogenesis of the free living nematode *C. elegans*. Comparative Biochemistry and Physiology 75B: 575–580.

Stebbins-Boaz, B., Hake, L. E., and Richter, J. D. (1996). CPEB controls the cytoplasmic polyadenylation of cyclin, Cdk2 and c-mos mRNAs and is necessary for oocyte maturation in *Xenopus*. EMBO Journal 5: 2582–2592.

Strome, S. (1986). Fluorescence visualization of the distribution of microfilaments in gonads and early embryos of the nematode *C. elegans*. Journal of Cell Biology 103: 2241–2252.

Sulston, J., and Hodgkin, J. (1988). Methods. In The Nematode *Caenorhabditis elegans*. W. B. Wood, editor, p. 587–606. Cold Spring Harbor Laboratory Press, Cold Spring Harbor, N.Y.

Swofford, D., "PAUP: Phylogenetic analysis using parsimony." Illinois National History Survey, Champaign (1993).

Vacquier, V. D., *Science* 281, 1995 (1998).

Veenstra, J. A. (2000). Mono- and dibasic proteolytic cleavage sites in insect neuroendocrine peptide precursors. Archives of Insect Biochemistry and Physiology 43: 49–63.

Ward, S. (1986). Asymmetric localization of gene products during the development of *C. elegans* spermatozoa. In Gametogenesis and the Early Embryo. 44th Symposium of the Society for Developmental Biology. Gall, J. G., (ed). p.55–75. Alan R. Liss, NY.

Ward, S., Argon, Y., and Nelson, G. A. (1981). Sperm morphogenesis in wild-type and fertilization-defective mutants of *C. elegans*. Journal of Cell Biology 91: 26–44.

Ward, S., Burke, D. J., Sulston, J. E., Coulson, A. R., Albertson, D. G., Ammons, D., Klass, M., and Hogan, E. (1988). Genomic organization of major sperm protein genes and pseudogenes in the nematode *Caenorhabditis elegans*. Journal of Molecular Biology 199, 1–13.

Ward, S., and Carrel, J. S. (1979). Fertilization and sperm competition in the nematode *Caenorhabditis elegans*. Developmental Biology 73: 304–321.

Ward, S., Hogan, E., and Nelson, G. A. (1983). The initiation of spermiogenesis in the nematode *C. elegans*. Developmental Biology 98: 70–79.

Ward, S., and Klass, M. (1982). The location of the major protein in *C. elegans* sperm and spermatocytes. Developmental Biology 92: 203–208.

Ward, S., and Miwa, J. (1978). Characterization of temperature-sensitive, fertilization-defective mutants of the nematode *C. elegans*. Genetics 88: 285–303.

Ward, S., Roberts, T. M., Strome, S., Pavalko, F. M., and Hogan, E. (1986). Monoclonal antibodies that recognize a polypeptide antigenic determinant shared by multiple *C. elegans* sperm-specific proteins. Journal of Cell Biology 102: 1778–1786.

Wimalawansa, S. J. (1995). Purification and biochemical characterization of Neuropeptide Y2 receptor. The Journal of Biological Chemistry 270: 18523–18530.

Wolf, N., Hirsh, D., and McIntosh, J. R. (1978). Spermatogenesis in males of the free-living nematode, *C. elegans*. Journal of Ultrastructure Research 63: 155–169.

Yasunaga, S., Grati, M., Cohen-Salmon, M., El-Amraoui, A., Mustapha, M., Salem, N., El-Zir, E., Loiselet, J., and Petit, C. (1999). A mutation in OTOF, encoding otoferlin, a FER-1-like protein, causes DFNB9, a nonsyndromic form of deafness.Nature Genetics 21:363–369.

Yew, N., Mellini, M. L., and Vande Woude, G. F. (1992). Meiotic initiation by the mos protein in *Xenopus*. Nature 355: 649–652.

Yung, Y., et al., *FEBS Lett.* 408, 292 (1997).

4. To prepare SCM, purified sperm (26) were incubated in M9 buffer (~5×10$^7$ sperm/ml) for 1–16 hrs at 20° C. Sperm were removed by centrifugation for 5 min at 14,000 rpm in an Eppendorf microcentrifuge (model 5415C) and filtration through a 0.22 μm cellulose acetate filter (Costar). Samples (~50 pl) were microinjected into the uterus of fog-2(q71) (3) adult females (30 hrs post-L4 at 20° C.). Following injection, females were anesthetized for 20 minutes with 0.1% tricaine/0.01% tetramisole (32) in M9. Oocyte maturation and sheath cell contraction rates were monitored by time-lapse video microscopy (1) for 70 minutes.

5. SCM or sperm lysates (by vortexing with glass beads) were fractionated on $C_4$ and $C_{18}$ columns (Vydac) using an acetonitrile gradient (0–100%) mobile phase. TFA (0.1%) was added to the mobile phase to sharpen peaks by ion pairing. Absorbance peaks (214 nm) were collected manually, dialyzed against M9, and bioassayed. Active fractions were analyzed by MALDI-TOF mass spectrometry using internal molecular weight standards (insulin, cytochrome C and myoglobin).

6. Post source decay mass spectrometry (33) of a 1960 Da peptide, generated by tryptic digestion of the active fraction, yielded the sequence IVFNAPYDDKHTYHIK, which matched MSP.

9. His-tagged MSP-77, MSP-38, and MSP(1-106) were expressed in *Escherichia coli* M15[pRep4] (Qiagen) and purified under native conditions by Ni-NTA affinity chromatography (>99% pure by SDS-PAGE and mass spectrometry). The extinction coefficient $\epsilon$ (275 nm) of MSP was estimated by amino acid analysis of a purified His-tagged MSP-77 standard. MSP concentrations were determined by amino acid hydrolysis, SDS-PAGE, and spectrophotometrically using $\epsilon$ (275 nm)=3.29×10$^4$M$^{-1}$ cm$^{-1}$.

10. Anti-MSP (26) or control EMB-30 antibodies (34) were injected (~40 µg/ml) into adult wild-type N2 hermaphrodites (24 hr post-L4 at 20° C.). The injected animals were cultured individually with food for a 3 hr time period and total ovulations were determined. The effect of antibody injection on oocyte maturation was determined by time lapse video microscopy. A two-sample t-test was used to compare results of MSP injections with controls.

12. The C-terminal MSP peptide (EWFQGDGMVRRKNLPIEYNP) was prepared by solid-phase synthesis and purified by HPLC (Research Genetics).

15. Diphosphorylated MAP kinase was detected in dissected and fixed (3% paraformaldehyde) gonadal preparations using indirect immunofluorescence with the antibody MAPK-YT (35) (Sigma). In *C. elegans* preparations, MAPK-YT only recognizes mpk-1 map kinase gene products (36). Gonads were stained 8, 40, or 50 min post MSP injection. Activated MAP kinase was detected 40 and 50 min post-injection but was not detectable 8 min post injection.

22. Phylogenetic analyses were performed using maximum parsimony and neighbor-joining methods. Amino acid sequences from MSP and MSP-like domains of several representative VAPs were used in the analyses. For parsimony, the heuristic search option of PAUP* 3.1 (37) was used for tree construction, with 200 random order taxon addition replicates and tree bisection and reconnection branch swapping. Bacterial PapD, which is structurally related to MSP, was used as the outgroup. The "protpars" matrix of PAUP* 3.1 was used to weigh amino acid substitutions. To obtain bootstrap values, 100 bootstrap replicates were performed using simple taxon addition with tree bisection and reconnection branch swapping.

The present invention is not limited by mechanism or theory. Although there have been described general and specific embodiments of the invention herein, these embodiments do not limit the scope of the invention except as set forth in the claims below.

What is claimed is:

1. The method of indentifying an anti-nematode agent comprising
    administering a test compound to a nematode;
    detecting a binding of the test compound to a major sperm protein of the nematode; and
    monitoring a female sexual maturation of the nematode, wherein inhibition of the female sexual maturation indicates that the test compound is the anti-nematode agent.

2. The method of claim 1, wherein monitoring the female sexual maturation of the nematode further comprises monitoring an oocyte meiotic maturation.

3. The method of claim 1, wherein monitoring the female sexual maturation of the nematode further comprises monitoring a gonadal sheath cell contraction.

4. The method of claim 1, wherein monitoring the female sexual maturation of the nematode further comprises monitoring an ovulation.

5. The method of claim 1, wherein monitoring the female sexual maturation of the nematode further comprises optical monitoring.

6. The method of claim 5, wherein optical monitoring further comprises optical monitoring by video microscopy.

7. The method of claim 5, wherein optical monitoring further comprises optical monitoring by fluorescent imaging.

8. The method of claim 1, wherein administering further comprises administering the test compound in combination with a pharmaceutically acceptable carrier.

9. A method of identifying an anti-nematode agent comprising:
    contacting a test compound to a major sperm protein polypeptide;
    detecting a composition wherein the composition is the test compound and the polypeptide;
    administering the test compound to a nematode; and
    monitoring a female sexual maturation of the nematode by optical monitoring.

10. The method of claim 9, wherein the polypeptide is SEQ ID NO: 2.

11. The method of claim 9, wherein monitoring the female sexual maturation of the nematode further comprises monitoring an oocyte meiotic maturation.

12. The method of claim 9, wherein monitoring the female sexual maturation of the nematode further comprises monitoring a gonadal sheath cell contraction.

13. The method of claim 9, wherein monitoring the female sexual maturation of the nematode further comprises monitoring an ovulation.

14. A method of identifying an anti-nematode agent comprising:
    affixing a test compound to a matrix;
    incubating the test compound with a major sperm protein polypeptide;
    washing the test compound to remove the major sperm protein polypeptide that is not bound to the test compound;
    detecting a composition wherein the composition is the test compound and the major sperm protein polypeptide;
    administering the test compound to a nematode; and
    observing a female sexual maturation of the nematode, wherein inhibiting the female sexual maturation indicates that the test compound is the anti-nematode agent.

15. The method of claim 14, wherein the major sperm protein polypeptide is labeled.

16. The method of claim 14, wherein observing the female sexual maturation of the nematode further comprises observing an oocyte meiotic maturation.

17. The method of claim 14, wherein observing the female sexual maturation of the nematode further comprises observing a gonadal sheath cell contraction.

18. The method of claim 14, wherein observing the female sexual maturation of the nematode further comprises observing an ovulation.

19. The method of claim 14, wherein the nematode is selected from a group consisting of: a fog-1 nematode, a fog-2 nematode, a fog-3 nematode, a fem-1 nematode, a fem-2 nematode, a fem-3 nematode, and a gld-1 nematode.

* * * * *

UNITED STATES PATENT AND TRADEMARK OFFICE
CERTIFICATE OF CORRECTION

PATENT NO. : 6,863,881 B2
DATED : March 8, 2005
INVENTOR(S) : David Greenstein and Michael A. Miller It is certified that error appears in the above-identified patent and that said Letters Patent is hereby corrected as shown below:

Column 1,
Line 3, insert -- This invention was made with government support under grant number D07043-25 awarded by the National Institute of Health.
The government has certain rights to this invention. --

Signed and Sealed this

Seventeenth Day of May, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,863,881 B2 | Page 1 of 1 |
| DATED | : March 8, 2005 | |
| INVENTOR(S) | : David Greenstein and Michael A. Miller | |

It is certified that error appears in the above-identified patent and that said Letters Patent is hereby corrected as shown below:

Column 1,
Line 3, insert -- This invention was made with government support under grant number DO7043-25 awarded by the National Institute of Health.

The government has certain rights to this invention. --

Signed and Sealed this

Twenty-second Day of November, 2005

JON W. DUDAS
*Director of the United States Patent and Trademark Office*